United States Patent
Imai et al.

(10) Patent No.: US 11,802,373 B2
(45) Date of Patent: *Oct. 31, 2023

(54) METHOD FOR EVALUATING DEGREE OF CLEANLINESS OF RECYCLED MATERIAL, METHOD FOR MANUFACTURING RECYCLED MATERIAL, AND METHOD FOR MANUFACTURING RECYCLED PULP FIBER

(71) Applicant: Unicharm Corporation, Ehime (JP)

(72) Inventors: Shigeo Imai, Kanonji (JP); Mitsuhiro Wada, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 561 days.

This patent is subject to a terminal disclaimer.

(21) Appl. No.: 16/771,736

(22) PCT Filed: Dec. 20, 2018

(86) PCT No.: PCT/JP2018/047121
§ 371 (c)(1),
(2) Date: Jun. 11, 2020

(87) PCT Pub. No.: WO2019/124527
PCT Pub. Date: Jun. 27, 2019

(65) Prior Publication Data
US 2020/0392669 A1    Dec. 17, 2020

(30) Foreign Application Priority Data

Dec. 20, 2017 (WO) .................. PCT/JP2017/045795
Mar. 30, 2018 (JP) ................... 2018-069434
Mar. 30, 2018 (JP) ................... 2018-069442

(51) Int. Cl.
*D21C 5/02* (2006.01)
*G01N 33/34* (2006.01)

(52) U.S. Cl.
CPC ........... *D21C 5/022* (2013.01); *G01N 33/343* (2013.01)

(58) Field of Classification Search
CPC .......... D21C 5/022; D21C 3/003; D21C 3/22; D21C 3/04; G01N 33/343; B09B 3/00
See application file for complete search history.

(56) References Cited

U.S. PATENT DOCUMENTS 5,202,422 A    4/1993  Hiatt et al.
5,685,953 A *  11/1997 Solinas .................. D21C 9/153
                                                            162/65

(Continued)

FOREIGN PATENT DOCUMENTS

EP    1847831 A1   10/2007
EP    2975392 A1    1/2016

(Continued)

OTHER PUBLICATIONS

English Translation of FR 2672314 A1 retrieved Jan. 10, 2023 from Espacenet (Year: 2023).*

(Continued)

*Primary Examiner* — Eric Hug
*Assistant Examiner* — Elisa H Vera
(74) *Attorney, Agent, or Firm* — Fredrikson & Byron, P.A.

(57) ABSTRACT

The objective of the present disclosure is to provide a method for easily evaluating the degree of cleanliness of recycled material derived from used sanitary products. The evaluation method according to the present disclosure has the following configuration. This method for evaluating a degree of cleanliness of recycled material derived from used sanitary products includes: a preparation step of preparing a dispersed aqueous solution in which the recycled material is dispersed in water; a separation step of subjecting the (Continued)

dispersed aqueous solution to centrifugal separation to separate the dispersed aqueous solution into a liquid component and a solid component; and a measuring step of measuring the concentration of protein in the liquid component using a protein measuring means.

6 Claims, 5 Drawing Sheets

(56) References Cited

U.S. PATENT DOCUMENTS

| | | | |
|---|---|---|---|
| 10,260,199 B2* | 4/2019 | Konishi | B09B 5/00 |
| 10,273,388 B1* | 4/2019 | Tillman | C09J 161/06 |
| 10,280,560 B2* | 5/2019 | Yamaguchi | D21C 3/04 |
| 10,626,554 B2* | 4/2020 | Konishi | B09B 3/00 |
| 10,773,421 B2* | 9/2020 | Konishi | B09B 3/00 |
| 10,960,577 B2* | 3/2021 | Konishi | D21C 5/02 |
| 11,053,638 B2* | 7/2021 | Konishi | B29B 17/02 |
| 11,131,061 B2* | 9/2021 | Konishi | B09B 5/00 |
| 2002/0142452 A1 | 10/2002 | Yang et al. | |
| 2010/0133197 A1 | 6/2010 | Langner | |
| 2014/0271721 A1* | 9/2014 | Walser | A23L 25/30 |
| | | | 435/7.92 |
| 2015/0136343 A1 | 5/2015 | Tausche et al. | |
| 2015/0291762 A1* | 10/2015 | Watanabe | A61F 13/15707 |
| | | | 428/401 |
| 2017/0107667 A1 | 4/2017 | Konishi et al. | |
| 2017/0321243 A1 | 11/2017 | Partti-Pellinen et al. | |
| 2019/0000698 A1 | 1/2019 | Konishi et al. | |

FOREIGN PATENT DOCUMENTS

| | | | |
|---|---|---|---|
| EP | 3238840 A1 | 11/2017 | |
| FR | 2672314 A1 * | 8/1992 | D21C 9/10 |
| JP | 2001047023 A | 2/2001 | |
| JP | 2001147185 A | 5/2001 | |
| JP | 2005112857 A | 4/2005 | |
| JP | 2014217835 A | 11/2014 | |
| JP | 2016000881 A | 1/2016 | |
| JP | 2017095855 A | 6/2017 | |
| JP | 2017113736 A | 6/2017 | |
| JP | 6161669 B2 | 7/2017 | |
| JP | 2017140619 A | 8/2017 | |
| WO | 2014007105 A1 | 1/2014 | |
| WO | 2014142229 A1 | 9/2014 | |
| WO | 2017110234 A1 | 6/2017 | |

OTHER PUBLICATIONS

Shigeo Imai et al., "Environmental Impact Assessment of Pulp Reuse by Recycling Used Paper Diapers: Environmental Assessment of diaper recycling", Environmental Solution Technology, Jul. 1, 2016, vol. 15, No. 4, Japan Industrial Publishing Co., Ltd., pp. 85-89, with English Translation, 19 pgs.

Sachiko Adachi et al., Green Converting, Paper diaper-paper diaper circular recycling: New recycling techniques that reduce greenhouse gases by a third, CONVERTECH, Feb. 15, 2016, vol. 44, No. 2, pp. 50-52, with English Translation, 13 pgs.

English Abstract for Japanese Publication No. JP 2016-000881 A, published Jan. 7, 2016, 1 pg.

English Abstract for Japanese Publication No. JP 2017-113736A, published Jun. 29, 2017, 1 pg.

Rouwenhorst R J et al., "Determination of protein concentration by total organic carbon analysis," Journal of Biochemical and Biophysical Methods, Amsterdam, NL, vol. 22, No. 2, Feb. 1, 1991, pp. 119-128.

English Abstract and Machine Translation for Japanese Publication No. JP2017-140619A, published Aug. 17, 2017, 13 pgs.

Extended European Search Report for European Patent Application No. 18892955.8, dated Apr. 23, 2021, 10 pgs.

English Abstract and Machine Translation for Japanese Publication No. JP 2001-047023 A, published Feb. 20, 2001, 6 pgs.

Unicharm Corporation, "Corporate Social Responsibility Report 2017", Corporate Social Responsibility Report, Environmental Reporting, Comprehensive report viewing site, pp. 22-24 with English machine translation dated May 11, 2017, 10 pages.

English Abstract and Translation for Japanese Publication No. JP 2017-95855 A, published Jun. 1, 2017, 17 pgs.

Yonghua Wang et al., "Food Analysis (Third Edition)", China Light Industry Press, p. 191 (Jul. 2017), 3 pgs., untranslated.

Yonghua Wang et al., "Food Analysis (Third Edition)", China Light Industry Press, p. 191 (Jul. 2017), 3 pgs. partial English translation.

Yide Qin at al., "Biochemistry and Molecular Biology Experiments", University of Science and Technology of China Press, pp. 116-121, (Jan. 2017), 8 pgs. untranslated.

Yide Qin at al., "Biochemistry and Molecular Biology Experiments", University of Science and Technology of China Press, pp. 116-121, (Jan. 2017), 14 pgs. partial English translation.

Hideaki Hanaki et al., "Examining methods of eliminating bacteria for recycling of used paper diapers," Journal of Infectious Diseases, 2016, vol. 90, No. 3, p. 395, Untranslated.

English translation of Hideaki Hanaki et al., "Examining methods of eliminating bacteria for recycling of used paper diapers," Journal of Infectious Diseases, 2016, vol. 90, No. 3, p. 395, 1 pg.

PCT International Search Report dated Feb. 14, 2019 for Intl. App. No. PCT/JP2018/047121, from which the instant application is based, 2 pgs.

Feature Topic 3: Environmentally Friendly Manufacturing, CSR Activity Report 2016, Unicharm Corporation, [online], May 9, 2016, [retrieval date: Feb. 5, 2019], Internet: http://www.unicharm.co.jp/csr-eco/report/uccsr2016_all.pdf, pp. 21-24.

English Abstract and Machine Translation for Japanese Publication No. 2014-217835 A, published Nov. 20, 2014, 32 pgs.

English Abstract for Japanese Publication No. 2005-112857 A, published Apr. 28, 2005, 2 pgs.

Jizu Wang et al., "Non-woven Fabric Product and Application and Design Thereof", China Textile & Apparel Press, p. 7-13, (Feb. 1994), untranslated.

Jizu Wang et al., "Non-woven Fabric Product and Application and Design Thereof", China Textile & Apparel Press, (Feb. 1994) Partial English machine translation, 5 pgs.

English Abstract and Machine Translation for Japanese Publication No. JP 2001-147185 A, published May 29, 2001, 11 pgs.

* cited by examiner

METHOD FOR EVALUATING DEGREE OF CLEANLINESS OF RECYCLED MATERIAL, METHOD FOR MANUFACTURING RECYCLED MATERIAL, AND METHOD FOR MANUFACTURING RECYCLED PULP FIBER

RELATED APPLICATIONS

This application is a 35 U.S.C. 371 national phase filing from International Application No. PCT/JP2018/047121, filed Dec. 1, 2018, which claims priority to Japanese Application No. 2018-106406, filed Jun. 1, 2018, Japanese Application No. 2017-212276, filed Nov. 1, 2018, and WO/Japanese Application No. PCT/JP2017/045795, filed Dec. 20, 2017, the contents of which are incorporated herein by reference.

FIELD

The present disclosure relates to a method of evaluating cleanliness of a recycled material from an used sanitary product, to a method of manufacturing a recycled material from an used sanitary product, to recycled pulp fibers obtained from an used sanitary product, and to a method of manufacturing recycled pulp fibers from pulp fiber-containing an used sanitary product.

BACKGROUND

Background Art 1

Methods for manufacturing recycled pulp fibers from an used sanitary product have been researched (see PTL 1, PTL 2, PTL 3, PTL 4 and PTL 5, for example).

PTL 6 describes regenerated fibers obtained by regenerating treatment of a sanitary product that contains cellulose pulp, where the amount of superabsorbent polymer (SAP) in the regenerated fibers is less than 10%.

Background Art 2

Manufacture of recycled pulp fibers from an used sanitary product has also been researched.

PTL 6 describes regenerated fibers obtained by regenerating treatment of a sanitary product that contains cellulose pulp, where the amount of superabsorbent polymer (SAP) in the regenerated fibers is less than 10%.

PTL 7 describes a method of recovering materials from fouled sanitary products containing a water-absorbent resin that has gelled by absorption of water, wherein the fouled sanitary products containing a water-absorbent resin that has gelled by absorption of water are pulverized and the pulverized sanitary products are dispersed in water containing a disinfectant, so that a portion of the contaminants adhering to the sanitary products are separated from the pulverized sanitary products.

CITATION LIST

Patent Literature

[PTL 1] Japanese Unexamined Patent Publication No. 2010-059586
[PTL 2] Japanese Unexamined Patent Publication No. 2012-081433
[PTL 3] Japanese Unexamined Patent Publication No. 2013-079396
[PTL 4] Japanese Unexamined Patent Publication No. 2013-111478
[PTL 5] Japanese Unexamined Patent Publication No. 2017-113736
[PTL 6] international Patent Publication No. WO2014/007105
[PTL 7] Japanese Unexamined Patent Publication No. 2009-73198

SUMMARY

Technical Problem

<Objective 1>

The present inventors have confirmed that there is a large difference in cleanliness between the recycled pulp fibers produced by the methods described in PTLs 1 to 5. From the viewpoint of promoting usage of recycled pulp fibers and of providing a feeling of assurance to users, it may be desirable to establish methods for easily evaluating the cleanliness of recycled pulp fibers.

In conventional "methods for manufacturing recycled pulp fibers from an used sanitary product", usually the focus is on recovering a specific material (such as recycled pulp fibers) from a sanitary product without including the other constituent materials, as in PTL 6, whereas quantitative evaluation of the amount of protein-containing components derived from body fluids among an used sanitary product has not been studied.

It is therefore an objective of this disclosure to provide a method of easily evaluating cleanliness of a recycled material obtained from an used sanitary product.

<Objective 2>

Because an used sanitary product includes body fluids, food residues and bacteria, when recycled pulp fibers recovered from an used sanitary product are to be used for purposes that involve contact with water, it is preferred for the recycled pulp fibers to release as little body fluid, food residue and bacteria into the water as possible when it contacts with the water.

However, the regenerated fibers described in PTL 6 are recycled pulp fibers that are recovered from a sanitary product without including other constituent materials, and therefore the amount of protein-containing components derived from body fluids is not reduced. The recovering method described in PTL 7 includes the use of a disinfectant for disinfection or sterilization of contaminating bacteria adhering to a sanitary product, but the amount of protein-containing components derived from body fluids is not reduced.

It is therefore another objective of this disclosure to provide recycled pulp fibers from an used sanitary product, that can be used for purposes involving contact with water, and that have a low amount of protein-containing components that are capable of eluting into water.

Solution to Problem

<Objective Solution Means 1>

The present inventors have devised a method of evaluating cleanliness of a recycled material from an used sanitary product, the method including a provision step of providing a dispersed aqueous solution having the recycled material dispersed in water, a separation step of separating the dispersed aqueous solution into a liquid component and a solid component by centrifugal separation, and a measurement step of measuring a concentration of protein in the liquid component by protein measurement means.
<Objective Solution Means 2>

The present inventors have also devised recycled pulp fibers from an used sanitary product, the recycled pulp fibers including an aqueous dispersion dispersing the recycled pulp fibers at a solid concentration of 5.0 mass %, at a protein concentration of 60 μg/mL or lower as measured by the Modified Lowry method.

Advantageous Effects Of Invention

<Effect 1>

In regard to objective 1, the method of the disclosure allows the cleanliness of a recycled material from an used sanitary product to be easily evaluated.
<Effect 2>

In regard to objective 2, the recycled pulp fibers obtained from an used sanitary product of the disclosure can be used for purposes involving contact with water, with a low amount of protein-containing components that are capable of eluting into water.

DESCRIPTION OF EMBODIMENTS

Figure 1:
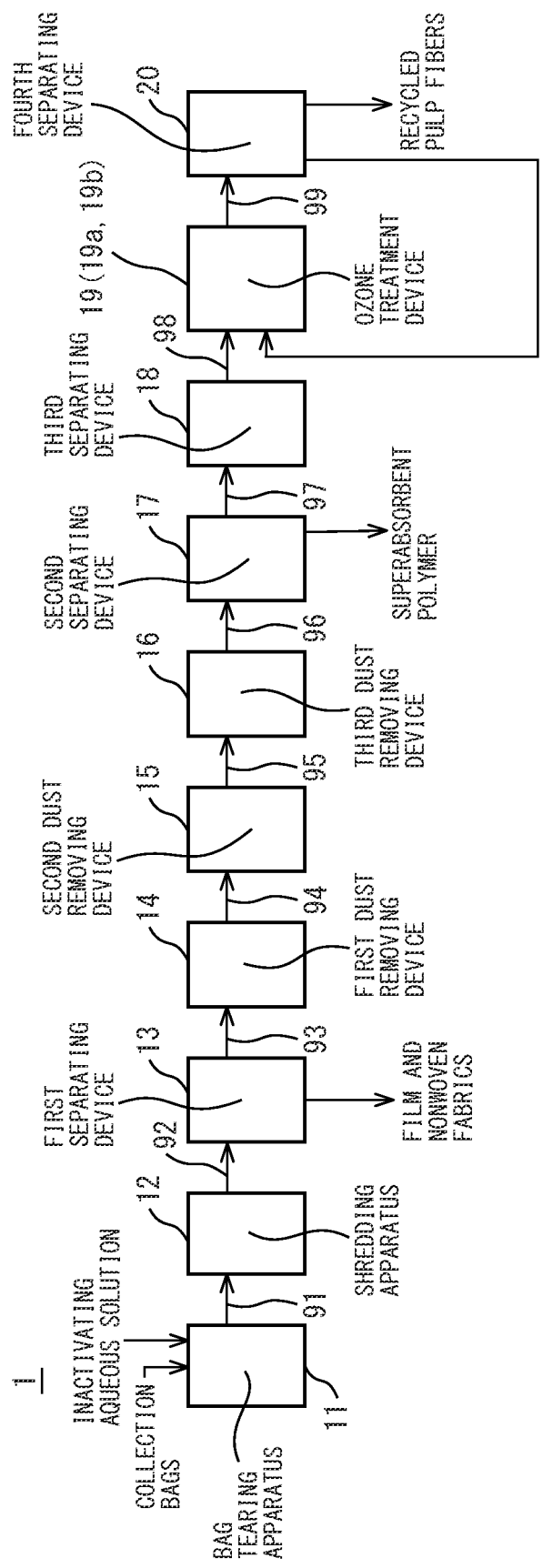
FIG. 1 is a block diagram showing system 1 according to a first embodiment.

Specifically, the present disclosure relates to the following aspects.
[Aspect 1]

A method of evaluating the cleanliness of a recycled material obtained from an used sanitary product, wherein the method comprises:

a provision step of providing a dispersed aqueous solution having the recycled material dispersed in water, a separation step of separating the dispersed aqueous solution into a liquid component and a solid component by centrifugal separation, and a measurement step of measuring a concentration of protein in the liquid component by protein measurement means.

When a recycled material, which is a recycled constituent material from an used sanitary product, contacts with water during use, a component derived from the used sanitary product, including body fluids (such as excreta and secretions), food residue and bacteria, preferably does not elute into the water. Such component contains proteins (these body fluids, food residues and bacteria will hereunder also be referred to as "protein-containing components").

This evaluation method allows easy measurement all at once of the amount of all of the protein-containing components that are capable of eluting into water from recycled material obtained from used sanitary product, when the recycled material has contacted with water.

The evaluation method can contribute to recycling of recycled material into a suitable article, according to amounts of protein-containing components, and in a method of manufacturing a recycled material it can contribute to controlling cleanliness and providing users of the recycled material with a feeling of assurance.
[Aspect 2]

The method according to aspect 1, which further includes, between the provision step and the separation step, a removal step of removing a constituent material of the sanitary product and/or the recycled material in the dispersed aqueous solution.

Since this evaluation method includes the predetermined removal step, the constituent material is less likely to have an effect when the protein is measured in the measurement step, and various protein measurement methods can be employed.
[Aspect 3]

The method according to aspect 1 or 2, wherein the used sanitary product includes pulp fibers, and the recycled material is recycled pulp fibers.

Virgin pulp fibers, which have high water absorption, are very commonly provided for purposes that involve contact with water, such as water-absorption purposes. Recycled pulp fibers likewise, similar, to virgin pulp fibers, are also highly valuable when they can be used for purposes that involve contact with water, and the market for recycling of pulp fibers is expected to further increase in the future.

In the evaluation method described above, since the recycled material is recycled pulp fibers and it is possible to easily measure the amount of a protein-containing component such as bacteria and body fluids that are capable of eluting into water, which are present in the recycled pulp fibers, it is possible to provide a consistent level of safety to the recycled material (recycled pulp fibers) that is evaluated.
[Aspect 4]

The method according to aspect 3, wherein a solid concentration of the dispersed aqueous solution is 5.0 mass %.

Since the solid concentration of the dispersed aqueous solution is within a predetermined range in this evaluation method, the ease of stirring of the aqueous dispersion is maintained while the protein-containing components in recycled pulp fibers tend to be more easily eluted into water.
[Aspect 5]

The method according to aspect 3 or 4, wherein the protein measurement means is a Modified Lowry method.

Since the protein concentration (amount of protein-containing components) is measured by a Modified Lowry method in this evaluation method, it is possible to easily measure the amount of protein-containing components in the recycled material.
[Aspect 6]

The method according to any one of aspects 3 to 5, wherein the recycled pulp fibers are produced by a manufacturing method that includes the following steps:

a supply step of supplying an aqueous solution containing the pulp fibers to a driving fluid supply port of a treatment tank provided with an ejector, the ejector comprising a driving fluid supply port, a mixed fluid discharge port connected to the treatment tank, and a suction fluid supply port between them, while supplying ozone to the suction fluid supply port, and a recycled pulp fiber-forming step of forming recycled pulp fibers by discharging a liquid mixture formed by mixing of the aqueous solution and the ozone in the ejector into the treatment solution in the treatment tank from the mixed fluid discharge port, and decomposing a protein-containing component in the pulp fibers.

Since recycled pulp fibers are produced by a predetermined manufacturing method in this evaluation method, the recycled pulp fibers have a high degree of cleanliness and it is possible to easily measure the amount of protein-containing components in the recycled pulp fibers.

[Aspect 7]

The method according to aspect 6, wherein the used sanitary product further include a superabsorbent polymer, the aqueous solution further includes the superabsorbent polymer in the supply step, and the superabsorbent polymer is further decomposed in the recycled pulp fiber-forming step.

Since the used sanitary product further includes a superabsorbent polymer while the recycled pulp fibers are produced by the predetermined manufacturing method in this evaluation method, the cleanliness of the recycled pulp fibers is high and there is a low amount of superabsorbent polymer or decomposed superabsorbent polymer that tends to be an inhibiting substance in the protein measurement means. This evaluation method therefore allows the amount of protein-containing components in recycled pulp fibers to be easily measured.

[Aspect 8]

The method according to aspect 7, wherein the manufacturing method includes, before the supply step, an inactivating step of inactivating the superabsorbent polymer by an acidic aqueous solution.

Since the method of manufacturing recycled pulp fibers includes the predetermined inactivating step for this evaluation, the ozone is less likely to be inactivated in the supply step or the recycled pulp fiber-forming step, and therefore the manufacturing method allows manufacture of recycled pulp fibers with low superabsorbent polymer or decomposed superabsorbent polymer, which tends to be an inhibiting substance in the protein measurement means, and with an extremely low amount of used sanitary product-derived protein-containing components that are capable of eluting into water. This evaluation method therefore allows the amount of protein-containing components in recycled pulp fibers to be easily measured.

[Aspect 9]

A method of manufacturing a recycled material from an used sanitary product, wherein the method includes:

a recycling step of forming the recycled material from the used sanitary product and an evaluation step of evaluating the cleanliness of the recycled material by the method according to any one of aspects 1 to 8.

In this manufacturing method it is possible to produce the recycled material with evaluated cleanliness, and thus to provide users of recycled material with a feeling of assurance.

[Aspect 10]

Recycled pulp fibers obtained from an used sanitary product, wherein:

an aqueous dispersion comprising the recycled pulp fibers dispersed at a solid concentration of 5.0 mass % contains protein at a concentration of 60 μg/mL or lower, as measured by a Modified Lowry method.

When a recycled material, which is a recycled constituent material recovered from used sanitary product, contacts with a liquid during use, a component derived from the used sanitary product, including body fluids (such as excreta and secretions), food residue and bacteria, preferably does not elute into the liquid. Bacteria have a particularly notable effect on the human body, and therefore recycled pulp fibers preferably do not contain bacteria originating from the used sanitary product.

Such components all contain proteins (these body fluids, food residues and bacteria, will hereunder also be referred to as "protein-containing, components").

Virgin pulp fibers, on the other hand, are highly likely to be supplied for water-absorption purposes due to their high water absorbing property, while recycled pulp fibers, similar to virgin pulp fibers, are also highly valuable as recycled pulp fibers if they can be used for water-absorption purposes, with the market for recycling of pulp fibers being expected to further increase in the future.

Since the recycled pulp fibers include a predetermined amount of protein capable of eluting into water, and specifically it includes an extremely small amount of the used sanitary product-derived protein-containing components that are capable of eluting into water, it can be used for purposes that involve contact with water, such as water-absorption purposes. The recycled pulp fibers can also provide a feeling of assurance for users using the recycled pulp fibers.

[Aspect 11]

Recycled pulp fibers according to aspect 10, wherein *Bacillus cereus* and *Bacillus subtilis* are not detected by a pour culture method, and/or *Bacillus* strains are not detected by a pour culture method.

*Bacillus* strains such as *Bacillus cereus* and *Bacillus subtilis* are resident flora generally present in soil, water and plants, and because they form spores, they are very highly durable bacteria. Spores are highly resistant to heat and disinfectants and often cannot be completely removed by common disinfection methods, in some rare cases even causing bacteremia, endocarditis, respiratory infection, food poisoning or eye infection.

When *Bacillus cereus* and *Bacillus subtilis* are not detected in the recycled pulp fibers by pour culture, they are unlikely to cause bacteremia, endocarditis, respiratory infection, food poisoning or eye infection, and the user can use the recycled pulp fibers without concern.

When *Bacillus* strains are not detected in the recycled pulp fibers by pour culture, they are unlikely to cause bacteremia, endocarditis, respiratory infection, food poisoning or eye infection, and the user can use the recycled pulp fibers without concern.

[Aspect 12]

The recycled pulp fibers according to aspect 10 or 11, wherein bacteria are not detected by a pour culture method and/or plate culture method.

When bacteria, and specifically general viable bacteria, are not detected by a pour culture method in the recycled pulp fibers, then the recycled pulp fibers can be used for water-absorption purposes that may involve animal contact. The user can also use the recycled pulp fibers without concern.

When bacteria, and specifically enterobacteria, are not detected in the recycled pulp fibers by plate culture, the recycled pulp fibers are unlikely to cause bacteremia, endocarditis, respiratory infection, food poisoning or eye infection, and the user can use the recycled pulp fibers without concern.

[Aspect 13]

Recycled pulp fibers according to any one of aspects 10 to 12, which have a $\Delta YI$ of 0 to 20 and/or a $\Delta W$ of 0 to 20, against a standard white board.

Pulp fibers in used sanitary product absorb excreta (such as feces and urine), often undergoing brown or yellow coloration. For reuse of pulp fibers in used sanitary product as recycled pulp fibers, therefore, it is necessary to bleach the coloration caused by excreta. Because recycled pulp fibers obtained from used sanitary product also generally create a feeling of psychological resistance in the user, it is preferable for recycled pulp fibers to have a high degree of whiteness from the viewpoint of reducing the feeling of psychological resistance in the user as well.

If the recycled pulp fibers have the predetermined ΔYI, or in other words, if it has whiteness at least equivalent to that of virgin pulp, then the user will have less of a feeling of psychological resistance to a product made using the recycled pulp fibers.

If the recycled pulp fibers have the predetermined ΔW or in other words, if it has whiteness at least equivalent to that of virgin pulp, then the user will have less of a feeling of psychological resistance to a product made using the recycled pulp fibers.

[Aspect 14]

A method of manufacturing recycled pulp fibers from a pulp fiber-containing used sanitary product, wherein the method includes:

a supply step of supplying an aqueous solution containing the pulp fibers to a driving fluid supply port of a treatment tank provided with an ejector, the ejector comprising the driving fluid supply port, a mixed fluid discharge port connected to the treatment tank, and a suction fluid supply port between them, while supplying ozone to the suction fluid supply port, and a recycled pulp fiber-forming step of forming recycled pulp fibers by discharging a liquid mixture formed by mixing of the aqueous solution and the ozone in the ejector into the treatment solution in the treatment tank from the mixed fluid discharge port, and decomposing the protein-containing components in the pulp fibers such that an aqueous dispersion comprising the recycled pulp fibers dispersed at a solid concentration of 5.0 mass % contains protein at a concentration of 60 μg/mL or lower, as measured by a Modified Lowry method.

This manufacturing method allows recycled pulp fibers to be manufactured which contains an extremely low amount of used sanitary product-derived protein-containing components that are capable of eluting into water. The method also allows manufacture of recycled pulp fibers that can be used for purposes that involve contact with water, such as water-absorption purposes. The manufacturing method also allows manufacture of recycled pulp fibers that can provide users with a feeling of assurance.

[Aspect 15]

The method according to aspect 14, wherein the used sanitary product further includes a superabsorbent polymer, the aqueous solution further includes the superabsorbent polymer in the supply step, and the superabsorbent polymer is further decomposed in the recycled pulp fiber-forming step.

With the manufacturing method described above it is possible to manufacture recycled pulp fibers that have reduced superabsorbent polymer and that contains an extremely low amount of used sanitary product-derived protein-containing components that are capable of eluting into water.

[Aspect 16]

The method according to aspect 15, wherein the manufacturing method includes, before the supply step, an inactivating step of inactivating the superabsorbent polymer by an acidic aqueous solution.

Since this manufacturing method includes the predetermined inactivating step, the ozone is less likely to be inactivated in the supply step and recycled pulp fiber-forming step, and therefore the manufacturing method allows manufacture of recycled pulp fibers with reduced superabsorbent polymer, and with an extremely low amount of used sanitary product-derived protein-containing components that are capable of eluting into water.

The method of evaluating cleanliness of a recycled material ("method of evaluating cleanliness of a recycled material" will also be referred to hereunder simply as "cleanliness evaluation method") and the method of manufacturing a recycled material from an used sanitary product ("method of manufacturing a recycled material from an used sanitary product" will also be referred to hereunder simply as "recycled material manufacturing method"), according to the present disclosure, will be described in detail below.

The recycled pulp fibers obtained from an used sanitary product ("recycled pulp fibers obtained from an used sanitary product" will also be referred to hereunder simply as "recycled pulp fibers") and the method of manufacturing recycled pulp fibers from a pulp fiber-containing used sanitary product ("method of manufacturing recycled pulp fibers from a pulp fiber-containing used sanitary product" will also be referred to hereunder simply as "method of manufacturing recycled pulp fibers"), according to the present disclosure, will also be described in detail below.

<Cleanliness Evaluation Method>

The method of evaluating cleanliness of recycled material according to the disclosure includes the following steps.

A provision step of providing a dispersed aqueous solution having the recycled material dispersed in water (this will also be referred to hereunder as "dispersed aqueous solution provision step").

A separation step of separating the dispersed aqueous solution into a liquid component and a solid component by centrifugal separation (this will also be referred to hereunder as "solid-liquid separation step").

A measurement step of measuring a concentration of protein in the liquid component by protein measurement means (this will also be referred to hereunder as "protein concentration measurement step").

The cleanliness evaluation method of the disclosure may also include the following additional step, between the dispersed aqueous solution provision step and the solid-liquid separation step.

A removal step of removing a constituent material of the sanitary product or the recycled material in the dispersed aqueous solution (this will also be referred to hereunder as "material removal step").

[Dispersed Aqueous Solution Provision Step]

In the provision step, a dispersed aqueous solution comprising a recycled material dispersed in water is provided.

By dispersing the recycled material in water it is possible to cause the protein-containing components adhering to the surfaces of the recycled material and the protein-containing components that have infiltrated inside the recycled material (for example, the recycled pulp fibers), to elute into water.

As used herein, "elution" means that components of interest migrate into an aqueous solution in any manner such as dissolution or dispersion.

The recycled material is constituent material of a sanitary product that is to be recycled. The recycled material may be completely recycled material or material that is being recycled.

Examples of such constituent material is liquid-permeable sheets, liquid-impermeable sheets and absorbent bodies, which include pulp fibers, superabsorbent polymers and core wraps.

Examples of recycled material is recycled liquid-permeable sheets, recycled liquid-impermeable sheets and recycled absorbent bodies, which include pulp fibers that have been recycled ("pulp fibers that have been recycled" will hereunder be referred to as "recycled pulp fibers"), superabsorbent polymers that have been recycled, and core wraps that have been recycled.

When the recycled material is in a dry state, the dispersed aqueous solution can be formed by immersing and agitating the recycled material in deionized water or tap water, for example.

When the recycled material is in a wetted state, such as when it is dispersed in water during recycling of the constituent material, for example, it can be used directly as the dispersed aqueous solution.

The aqueous dispersion may contain the recycled material in any desired amounts.

When the recycled material is recycled pulp fibers, the aqueous dispersion includes the recycled pulp fibers at a solid concentration of 5.0 mass %. This will facilitate agitation of the aqueous dispersion while also aiding elution of the protein-containing components in the recycled pulp fibers into water.

This solid concentration, incidentally, assumes that the aqueous dispersion also includes impurities other than the recycled pulp fibers.

When the recycled material is not recycled pulp fiber, the aqueous dispersion may contain the recycled material at a solid concentration which is with the entirety of the recycled material immersed in water, and the aqueous dispersion may include the recycled material at a solid concentration of preferably 0.1 to 30.0 mass %, more preferably 0.5 to 20.0 mass % and even more preferably 1.0 to 10.0 mass %.

This solid concentration, incidentally, assumes that the aqueous dispersion also includes impurities other than the recycled material.

For the purpose of the present specification, the solid content and solid concentration can be measured by the formula:

Solid content (mass %) or solid concentration (mass %)=100×$m_1$/$m_0$ using $m_0$ (g) for the sample (recycled material and aqueous dispersion), and $m_1$ (g) for the residue obtained after drying the sample at 105° C. for 16 hours.

In order for the aqueous dispersion to have the water-elutable protein-containing components held by the recycled material dispersed in water, the aqueous dispersion is preferably agitated before the solid-liquid separation step, at preferably 100 to 1,500 rpm and more preferably 250 to 800 rpm, for preferably 5 to 30 minutes and more preferably 10 to 20 minutes.

[Material Removal Step]

The constituent material removal step is an optional step in which the recycled material or constituent material of a sanitary product in the dispersed aqueous solution is removed. This will allow the subsequent solid-liquid separation step to be carried out more easily, so that the protein measurement means will be less likely to be affected by the recycled material or constituent material of the sanitary product in the protein concentration measurement step.

The material removal step can be carried out by passing the dispersed aqueous solution through a filter, such as a mesh filter, for example, which is not particularly restricted and may be any one that allows the protein-containing components in the dispersed aqueous solution to pass through without allowing the recycled material or constituent material in the sanitary product to pass through.

When the recycled material is recycled pulp fiber, for example, the recycled pulp fibers themselves may be removed, or the constituent material other than the recycled pulp fibers may be removed.

It is not necessary to remove the entire amounts of recycled material or constituent material in the material removal step, incidentally. This is because the liquid components and solid components will be separated in the subsequent solid-liquid separation step.

[Solid-Liquid Separation Step]

In the solid-liquid separation step, the dispersed aqueous solution is centrifugally separated for separation into liquid components and solid components. This can inhibit the effect that the solid components, and specifically the constituent material in the sanitary product, will have on measurement in the subsequent protein concentration measurement step.

Any centrifuge that is known in the technical field may be used for the solid-liquid separation step, an example of such a centrifuge being Micro Refrigerated Centrifuge Model 3740 by Kubota Corp.

There are no particular restrictions on the rotational speed or time in the solid-liquid separation step so long as the dispersed aqueous solution can be separated into its liquid components and solid components, and they may vary depending on the specific gravity of the recycled material (constituent material).

When the recycled materials are recycled pulp fiber, centrifugal separation of the dispersed aqueous solution in the solid-liquid separation step is carried out under conditions with a rotational speed of preferably 3,000 to 15,000 rpm and more preferably 5,000 to 13,000 rpm, for a time period of preferably 1 to 50 minutes and more preferably 5 to 15 minutes, and at a temperature of preferably higher than 0° C. and 25° C. or lower, more preferably 2° C. to 10° C. and even more preferably 4° C. This will make recycled pulp fibers fragments less likely to be included in the liquid components, making the protein concentration measurement less likely to be affected by the recycled pulp fibers in the subsequent protein concentration measurement step.

Even when the recycled material is a material other than recycled pulp fibers (for example, when the recycled material is torn liquid-impermeable sheets), centrifugal separation is preferably carried out under the same conditions as when the constituent material is recycled pulp fibers. Since recycled material obtained from an used sanitary product usually has adhering pulp fibers fragments originating from the (recycled) pulp fiber, it is preferred to carry out centrifugal separation for accurate measurement of the protein concentration.

[Protein Concentration Measurement Step]

In the protein concentration measurement step, a concentration of protein in the liquid component is measured by protein measurement means.

The protein measurement means is not particularly restricted so long as it is means allowing measurement of the protein-containing components, and specifically body fluids (for example, excreta or secretions), food residues and bacteria, that may be present in an used sanitary product, but it is preferably means that allows measurement of body fluids (such as excreta or secretions), food residues and bacteria all at once.

Examples of such protein measurement means include the Modified Lowry method (hereunder also referred to as "ML method"), the Coomassie method and the Micro BCA method.

The Modified Lowry method is preferred because it is less affected by the nonwoven fabrics, films, pulp fibers and superabsorbent polymers that are constituent material of a sanitary product.

An example of a kit for carrying out the Modified Lowry method is the Modified Lowry Protein Assay Kit by Thermo Fisher Scientific Co.

The Coomassie method is prone to false positives, i.e. the effects of decomposed superabsorbent polymers, and especially decomposed acrylic acid-based superabsorbent polymers, and is therefore preferably used for measurement of protein concentrations in recycled material (constituent material) that does not contain superabsorbent polymers, such as recycled material (constituent material) other than superabsorbent polymers.

An example of a kit for carrying out the Coomassie method is the Coomassie (Bradford) Protein Assay Kit by Thermo Fisher Scientific Co.

The Micro BCA method is prone to false negatives, i.e. the effects of chelating agents such as citric acid, and is therefore preferably used for measurement of protein concentrations in recycled material (constituent material) that does not contain chelating agents.

An example of a kit for carrying out the Micro BCA method is the Micro BCA Protein Assay Kit by Thermo Fisher Scientific Co.

Since methods for measurement of protein concentrations using the Modified Lowry method. Coomassie method and Micro BCA method are publicly known they will not be described here.

For the cleanliness evaluation method of this disclosure, the recycled material may have any protein concentration, depending on the purpose of use. For example, when the recycled material is to be used for purposes that involve less likely to contact with water, such as building material, the aqueous dispersion comprising the recycled material dispersed at a solid concentration of 5.0 mass % may include protein at a converted concentration of 2,000 μg/mL or lower, 1,500 μg/mL or lower or 1,000 μg/mL or lower, for example.

When the recycled material in the cleanliness evaluation method of the disclosure is to be used for purposes involving contact with water, such as water-absorption purposes, the aqueous dispersion comprising the recycled material dispersed at a solid concentration of 5.0 mass % includes protein at a converted concentration of preferably 150 μg/mL or lower, more preferably 100 or lower, even more preferably 60 μg/mL or lower, yet more preferably 40 μg/mL or lower and even yet more preferably 7 μg/mL or lower. As a result, the recycled material will have an extremely low amount of used sanitary product-derived protein-containing components that are capable of eluting into water, thus providing a feeling of assurance for users that use the recycled pulp material.

The converted concentration is the converted concentration $C$ (μg/mL) calculated by the following formula:

$$C(\mu g/mL)=B\times(5.0/A),$$

when an aqueous dispersion comprising a recycled material dispersed at a solid concentration of $A$ (mass %) contains protein at a concentration of $B$ (μg/mL).

For example, when an aqueous dispersion containing a recycled material dispersed at a solid concentration of 10.0 mass % includes protein at a concentration of $D$ (μg/mL), the converted concentration $C$ (μg/mL) is 0.51 (μg/mL), and when an aqueous dispersion containing a recycled material dispersed at a solid concentration of 1.0 mass % includes protein at a concentration of $E$ (μg/mL), the converted concentration $C$ (μg/mL) is 5.0 $E$ (μg/mL).

<Recycled Material Manufacturing Method>

The method of manufacturing the recycled material from the used sanitary product according to the disclosure includes the following steps.

A recycling step of forming the recycled material from the used sanitary product (hereunder also referred to as "recycling step").

An evaluation step of evaluating the cleanliness of the recycled material by a predetermined cleanliness evaluation method (hereunder also referred to as "evaluation step").

[Recycling Step]

In the recycling step, a recycled material is formed from an used sanitary product.

There are no particular restrictions on the specific means used to form the recycled material from the used sanitary product, and any recycling means known in the technical field may be employed.

For example. When the recycled material is superabsorbent polymers, the means for recycling the superabsorbent polymers may be the one described in Japanese Unexamined Patent Publication No. 2013-198862, Japanese Unexamined Patent Publication No. 2003-326161 or Japanese Unexamined Patent Publication No. 2003-225645.

When the recycled material is liquid-impermeable sheets, the means for recycling the liquid-impermeable sheets may be the one described in PTL 2, Japanese Unexamined Patent Publication No. 2001-47023 or Japanese Unexamined Patent Publication No. 2010-230807.

When the recycled material is recycled pulp fibers (pulp fibers), the means for recycling the pulp fibers may be the one described in PTL 1, PTL 3, PTL 5 or PTL 6.

When the recycled material is recycled pulp fibers (pulp fibers), the recycled pulp fibers can be manufactured according to the following embodiments.

First Embodiment

For the first embodiment, used sanitary products to be recycled are collected or obtained from an outside source, a mixture of pulp fibers and superabsorbent polymer is separated from the collected used sanitary products, and the separated mixture is used for manufacture of recycled pulp fiber. Several of the used sanitary products are gathered together and enclosed and collected in collecting bags (hereunder also referred to as "collection bags"), so that excreta and bacteria do not leak out. Each of the used sanitary products is rolled or folded with the front sheet facing inward so that odors and excreta do not diffuse to the surroundings.

A system 1 to be used in the method of manufacturing recycled pulp fibers from a mixture of pulp fibers and superabsorbent polymer separated from used sanitary products will now be described. The system 1 is a system for recovering pulp fibers from used sanitary products to manufacture recycled pulp fiber. FIG. 1 is a block diagram showing an example of the system 1 according to the first embodiment. The system 1 comprises an ozone treatment device 19, and preferably a bag tearing apparatus 11, a shredding apparatus 12, a first separating device 13, a first dust removing device 14, a second dust removing device 15, a third dust removing device 16, a second separating device 17, a third separating device 18 and a fourth separating device 20.

The bag tearing apparatus 11 opens holes in the collection bags enclosing the used sanitary products, while they are in an inactivating aqueous solution. The bag tearing apparatus 11 comprises a solution tank, a stirrer and a shredding blade, for example. The solution tank stores an inactivating aqueous solution. The stirrer is provided in the solution tank, and it agitates the inactivating aqueous solution to create a swirl flow. The shredding blade is provided at the bottom of the solution tank, and it opens holes in the collection bags that have been drawn downward in the inactivating aqueous solution inside the solution tank by the swirl flow. An "inactivating aqueous solution" is an aqueous solution that inactivates the superabsorbent polymer. Inactivation lowers the water absorption capacity of the superabsorbent polymer. As a result, the superabsorbent polymer discharges water until reaching the amount permitted by the water absorption capacity, i.e. it is dewatered. An example of using an acidic aqueous solution as the inactivating aqueous solution will now be explained.

The shredding apparatus 12 shreds the used sanitary products in the acidic aqueous solution together with their collection bags. The shredding apparatus 12 includes a shredder and a pump, for example. The shredder is connected with the solution tank, and it shreds the used sanitary products in the collection bags that have been fed out from the solution tank with the acidic aqueous solution (liquid mixture 91), together with their collection bags in the acidic aqueous solution. The shredder may be a twin-screw shredder (for example, a twin-screw rotary shredder, twin-screw differential shredder or twin-screw shearing shredder), and specifically it may be a SUMICUTTER (product of Sumitomo Heavy Industries Environment Co. Ltd.). The pump is connected to the downstream end of the shredder, and it draws out the shredded matter obtained by the shredder from the shredder, together with the acidic aqueous solution (liquid mixture 92), and feeds it to the following step. The shredded matter contains pulp fibers and superabsorbent polymer, and also other material (such as the collection bag materials, films, nonwoven fabrics and elastic solids).

The first separating device 13 agitates the liquid mixture 92 containing the shredded matter obtained from the shredding apparatus 12 and the acidic aqueous solution, removing the contaminants such as excreta from the shredded matter while separating the pulp fibers, superabsorbent polymer and acidic aqueous solution (liquid mixture 93) from the liquid mixture 92, and feeds it to the first dust removing device 14. The first separating device 13 may be, for example, a washing machine comprising a washing tank/dewatering tank and a water tank surrounding it, a specific one being an ECO-22B horizontal washing machine (product of Inax Corp.). The washing tank/dewatering tank (rotating drum) is used as a washing tank/sifting tank (separation tank).

The first dust removing device 14 separates the acidic aqueous solution containing the pulp fibers and superabsorbent polymer (liquid mixture 93), which has been fed out from the first separating device 13, into the pulp fibers and superabsorbent polymer in the acidic aqueous solution (liquid mixture 94) and the other material (contaminants), using a screen with a plurality of openings. The pH of the acidic aqueous solution is preferably kept within a predetermined range from the viewpoint of inactivation of the superabsorbent polymer (including adjustment of its size and specific gravity). The predetermined range is a range of pH variation within ±1.0, and the adjustment may be by addition of an acidic solution as necessary. The first dust removing device 14 may be, for example, a screen separator, and specifically a Pack Pulper (product of Satomi Seisakusho).

The second dust removing device 15 separates the acidic aqueous solution containing the pulp fibers and superabsorbent polymer (liquid mixture 94), which has been fed out from the first dust removing device 14, into the pulp fibers and superabsorbent polymer in the acidic aqueous solution (liquid mixture 95) and the other material (contaminants), using a screen with a plurality of openings. The pH of the acidic aqueous solution is preferably kept within a predetermined range as specified above. The second dust removing device 15 may be, for example, a screen separator, and specifically a Lamo Screen (by Aikawa Iron Works Co.).

The third dust removing device 16 separates the acidic aqueous solution containing the pulp fibers and superabsorbent polymer (liquid mixture 95), which has been fed out from the second dust removing device 15, into the pulp fibers and superabsorbent polymer in the acidic aqueous solution (liquid mixture 96) and the other material (high specific gravity contaminants), by centrifugal separation. The pH of the acidic aqueous solution is preferably kept within a predetermined range as specified above. The third dust removing device 16 may be, for example, a cyclone separator, and specifically an ACT Low Concentration Cleaner (by Aikawa Iron Works Co.). The acidic aqueous solution containing the pulp fibers and superabsorbent polymer (liquid mixture 95) is supplied into an inverted conical case of the third dust removing device 16 at a predetermined flow rate, so that the relatively light specific gravity pulp fibers and superabsorbent polymer in the acidic aqueous solution rise while the heavier specific gravity contaminants (such as metals) fall.

The second separating device 17 separates the acidic aqueous solution containing the pulp fibers and superabsorbent polymer (liquid mixture 96), which has been fed out from the third dust removing device 16, into pulp fibers in the acidic aqueous solution (liquid mixture 97) and superabsorbent polymer in the acidic aqueous solution, using a screen with a plurality of openings. The second separating device 17 may be, for example, a drum screen separator, and specifically a Drum Screen Dewaterer (by Toyo Screen Kogyo Co., Ltd.).

The third separating device 18, using a screen with a plurality of openings, separates the pulp fibers that has been fed out from the second separating device 17, the inseparable remaining superabsorbent polymer and the acidic aqueous solution (liquid mixture 97), into solid including the pulp fibers and superabsorbent polymer (mixture 98) and liquid including the superabsorbent polymer and acidic aqueous solution, while applying pressure to the solid portion to crush the superabsorbent polymer in the solid. The third separating device 18 may be a screw press dewaterer, for example, and specifically a screw press dewaterer (by Kawaguchi Seiki Co., Ltd). The third separating device 18 feeds out liquid including the superabsorbent polymer and acidic aqueous solution from the slits on the side walls of the drum screen, and feeds out the solid matter including the pulp fibers and superabsorbent polymer from the cover gap where the pressing force of the drum screen tip has been adjusted. While crushing the superabsorbent polymer. The pressure force applied onto the cover may be 0.01 MPa or higher and 1 MPa, or lower.

The ozone treatment device 19 treats the pulp fibers including the crushed superabsorbent polymer in the solid (mixture 98) that has been fed out from the third separating device 18, with ozone. The superabsorbent polymer is thus oxidatively decomposed, dissolved in the treatment solution and removed from the pulp fibers, and the recycled pulp fibers that no longer contain the superabsorbent polymer are fed out together with the treatment solution (liquid mixture 99). The ozone treatment device 19 also decomposes the protein-containing, components in the recycled pulp fibers (pulp fibers) and removes the protein-containing components that are capable of eluting into water.

Figure 2:
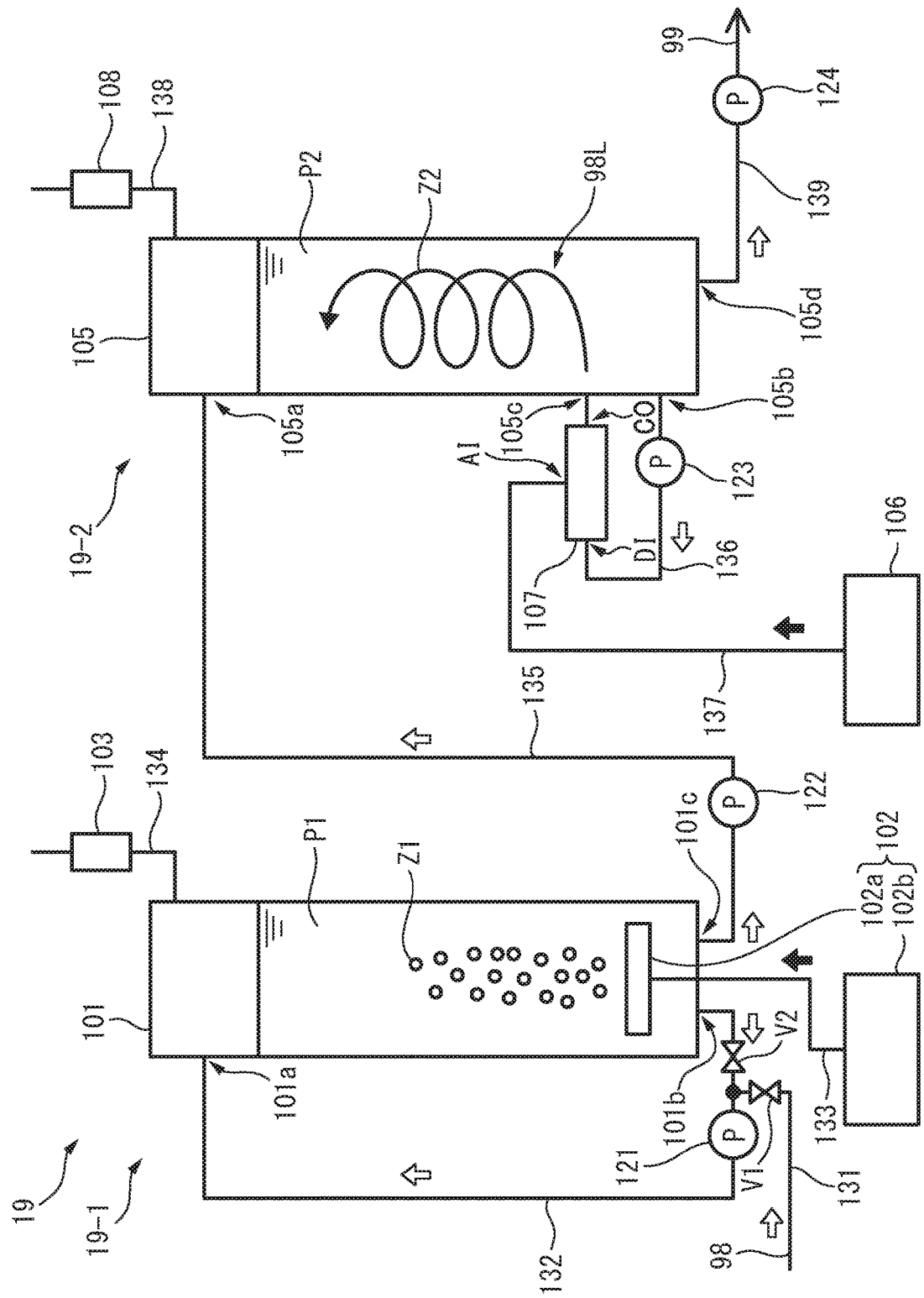
FIG. 2 is a schematic diagram of an ozone treatment device 19.

FIG. 2 is a schematic diagram of an ozone treatment device 19. The ozone treatment device 19 comprises a pretreatment apparatus 19-1 and a treatment apparatus 19-2. The pretreatment apparatus 19-1 removes at least a portion of the superabsorbent polymer from the pulp fibers in the mixture 98. This lowers the viscosity of the superabsorbent polymer-containing pulp fibers in the mixture 98. The treatment apparatus 19-2 further removes superabsorbent polymer from the pulp fibers of the mixture 98, which has had at least a portion of the superabsorbent polymer removed and its viscosity lowered by the pretreatment apparatus 19-1.

The pretreatment apparatus 19-1 comprises a pretreatment tank 101, an ozone dissipating apparatus 102, a pump 122 (pretreatment solution transfer unit), a pump 121 (pretreatment solution circulating unit) and an ozone decomposer 103.

The pretreatment tank 101 is a tank containing pretreatment solution P1. The pretreatment solution P1 is initially water, for example, with the ozone Z1 for pretreatment (described below) becoming dissolved in it as treatment proceeds in the pretreatment apparatus 19-1, or the ozone Z1 may be dissolved in it beforehand.

The ozone dissipating apparatus 102 is an apparatus for dissipation of the ozone Z1 for pretreatment into the pretreatment solution P1 in the pretreatment tank 101, and it includes an ozone dissipating unit 102a and an ozone generating unit 102b. The ozone generating unit 102b generates ozone Z1 for pretreatment, which is to decompose the superabsorbent polymer into a form that is soluble in the pretreatment solution P1.

The ozone dissipating unit 102a is provided in the pretreatment tank 101, and in the pretreatment solution P1, it dissipates the ozone Z1 for pretreatment at the lower end of the mixture 98, toward the mixture 98 (pulp fibers containing superabsorbent polymer) that has separated from the base of the pretreatment tank 101 and is present in the pretreatment solution P1. The ozone Z1 is dissipated in the form of numerous fine bubbles, for example. This allows the superabsorbent polymer in the mixture 98 to oxidatively decompose and to dissolve in the pretreatment solution P1. In other words, the superabsorbent polymer in the pulp fibers is reduced and the viscosity of the superabsorbent polymer-containing pulp fibers is lowered.

The pump 122 (pretreatment solution transfer unit) is provided along piping 135 that connects an outlet 101c provided at the bottom of the pretreatment tank 101 and a supply port 105a provided at the top of the treatment tank 105 (described below) of the treatment apparatus 19-2. The pump 122 extracts at least a portion of the pretreatment solution P1 containing the mixture 98 with reduced superabsorbent polymer in the pretreatment tank 101, from the bottom of the pretreatment tank 101, and transfers it to a treatment solution P2 through the top of the treatment tank 105.

The pump 121 (pretreatment solution circulating unit) is provided along piping 132 that connects an outlet 101b provided at the bottom of the pretreatment tank 101 and a supply port 101a provided at the top of the pretreatment tank 101. The pump 121 extracts at least a portion of the pretreatment solution P1 containing the mixture 98 from the bottom of the pretreatment tank 101, and supplies it from the top of the pretreatment tank 101 into the pretreatment solution P1. The pump 121 receives an aqueous solution in which the mixture 98 and water are mixed, through piping 131, 132, and supplies it from the supply port 101a to the pretreatment tank 101 through the piping 132. Circulation of the liquid through the piping 131, 132 is controlled by a valve V1 in the piping 131 and a valve V2 in the piping 132.

The ozone decomposer 103 receives the ozone Z1 that has accumulated at the top of the pretreatment tank 101 through the piping 134, decomposes and detoxifies the ozone, and discharges it to the outside.

The pretreatment solution P1 in the pretreatment tank 101 is initially the pretreatment solution P1 alone, with the mixture 98 and the pretreatment ozone Z1 later becoming mixed with the initial pretreatment solution P1 as the treatment proceeds, but for the first embodiment these will be collectively referred to as the pretreatment solution P1.

The treatment apparatus 19-2 comprises the treatment tank 105, an ozone supply apparatus (ozone supply unit) 106, an ejector 107, a pump 123 (aqueous solution supply unit and treatment solution circulating unit), a pump 124 and an ozone decomposer 108.

The treatment tank 105 is a tank that contains the treatment solution P2, and it is preferably circular tubular from the viewpoint of more easily creating a swirl flow in the treatment solution P2 by the liquid mixture 98L (described below) discharged from the ejector 107. The treatment solution P2 is initially water, for example, but as treatment in the treatment apparatus 19-2 proceeds the treatment ozone Z2 (described below) dissolves in it, and as treatment in the pretreatment apparatus 19-1 proceeds, it contains the pretreatment solution P1 that includes the mixture 98 (superabsorbent polymer and pulp fibers). Ozone Z2 may also be dissolved in it beforehand.

The ozone supply apparatus 106 generates ozone Z2 that is to decompose the superabsorbent polymer so that it can dissolve in the treatment solution P2, and supplies it to the ejector 107.

The pump 123 (aqueous solution supply unit and treatment solution circulating unit) supplies the ejector 107 with the aqueous solution that includes the mixture 98 of the superabsorbent polymer and pulp fiber. The pump 123 is provided along the piping 136, the piping 136 connecting the outlet 105b that is at the bottom of the treatment tank 105 and the supply port 105c that is at the bottom of the treatment tank 105 and above the outlet 105b. The piping 136 near the supply port 105c is preferably directed slightly upward, from the viewpoint of helping the liquid mixture 98L discharged from the ejector 107 to cause rising of the swirl flow formed in the treatment solution P2.

The ejector 107 (aspirator) is provided along the piping 136, and it has a driving fluid supply port DI, a suction fluid supply port AI and a mixed fluid discharge port CO. The ejector 107 causes the driving fluid to flow from the driving fluid supply port DI to the mixed fluid discharge port CO, creating a state of reduced pressure in a narrow segment of the flow path by the Venturi effect, whereby a suction fluid is drawn up into the narrow segment through the suction fluid supply port AI and mixed with the driving fluid, and then discharged through the mixed fluid discharge port CO as a mixed fluid.

The treatment solution P2 containing the superabsorbent polymer and pulp fibers (mixture) in the treatment tank 105 is supplied to the driving fluid supply port D1 by the pump 123, and flows toward the mixed fluid discharge port CO. At the same time, the ozone Z2 from the ozone supply apparatus 106 is drawn in from the suction fluid supply port AI into the ejector 107. This results in mixing of the ozone Z2 with the treatment solution P2 that includes the superabsorbent polymer and pulp fibers, and discharge as a liquid mixture 98L from the mixed fluid discharge port CO into the treatment tank 105. In the discharged liquid mixture, the superabsorbent polymer is oxidatively decomposed by the ozone Z2 while being removed, and swirls in the treatment tank 105, gradually rising upward while the treatment solution P2 is agitated.

The pump 124 is provided along the piping 139 whereby the outlet 105d provided at the bottom of the treatment tank 105 is connected with later-stage devices (not shown). The pump 124 extracts at least a portion of the treatment solution P2 containing the mixture 98 from which the superabsorbent polymer has been removed, which is in the treatment tank 105, from the bottom of the treatment tank 105, and transfers it to the later-stage devices.

The ozone decomposer 108 receives the ozone Z2 that has accumulated at the top of the treatment tank 105 through piping 138, decomposes and detoxifies the ozone Z2, and discharges it to the outside.

The treatment solution P2 in the treatment tank 105 is initially the treatment solution P2 alone, with the mixture and ozone later becoming mixed with the initial treatment solution P2 as the treatment proceeds, but for the first embodiment these will be collectively referred to as the treatment solution P2.

The treatment apparatus 19-1 and treatment apparatus 19-2 are used together in the ozone treatment device 19 for the following reason. From the viewpoint of treatment efficiency, it is better to use only the treatment apparatus 19-2 comprising the ejector 107. However, if the aqueous solution containing the mixture 98, which is supplied to the ozone treatment device 19, has a high concentration of superabsorbent polymer adhering to the pulp fibers, then the viscosity of the mixture 98 will increase and the ejector 107 can potentially become clogged. For the first embodiment, this is dealt with by first treating the aqueous solution containing the mixture 98 in the treatment apparatus 19-1, thus helping to lower the viscosity of the mixture 98, i.e. to easily reduce the superabsorbent polymer, to a degree such that the ejector 107 is not clogged. The protein-containing components in the recycled pulp fibers (pulp fibers) are also decomposed, which helps the protein-containing components that are capable of eluting into water to be easily removed from the recycled pulp fibers (pulp fibers).

The fourth separating device 20 then separates the treatment solution containing the pulp fibers that has been treated by the ozone treatment device 19 (liquid mixture 99), into treatment solution and pulp fibers, using a screen with a plurality of openings. The recycled pulp fibers are recovered as a result.

Figure 3:
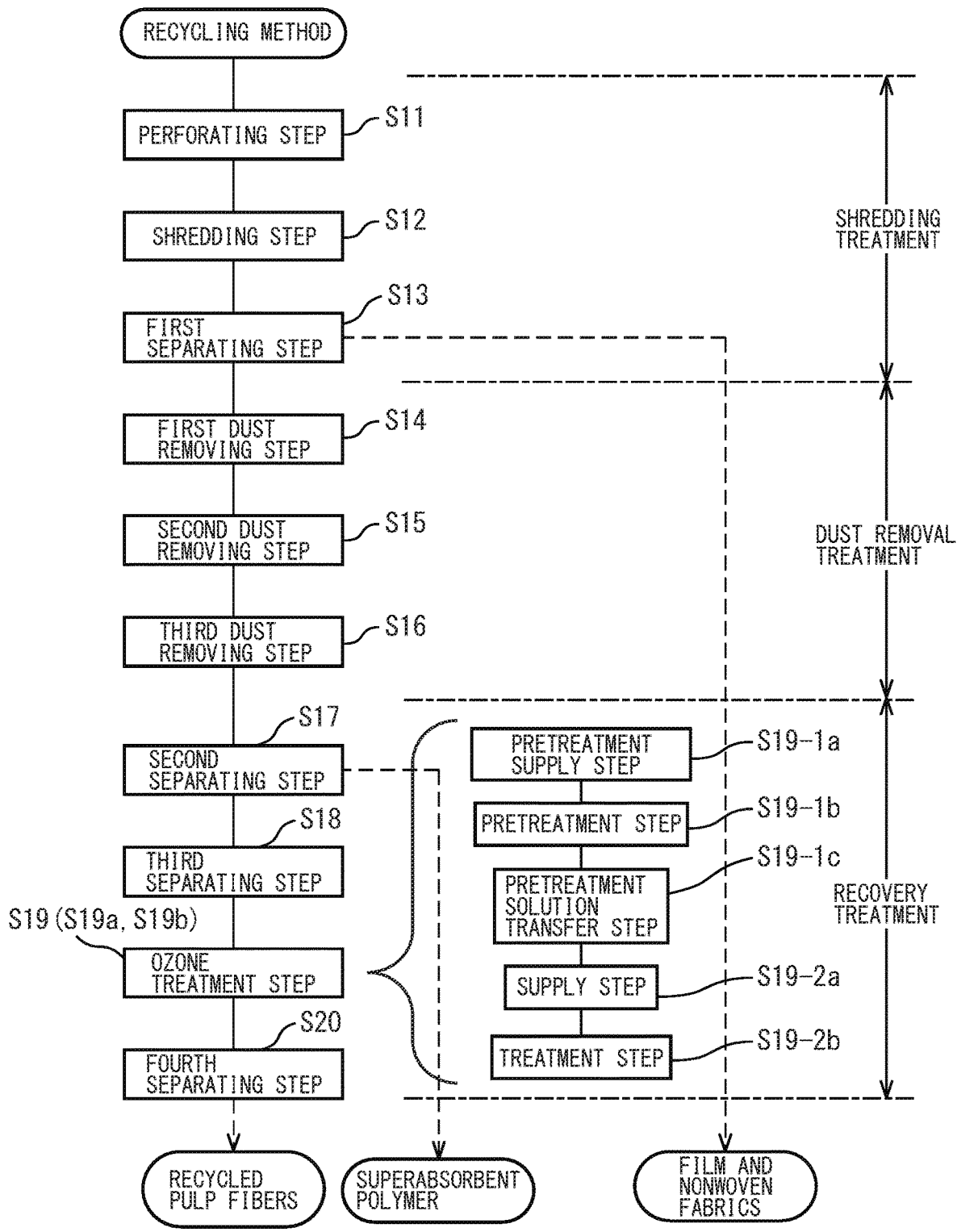
FIG. 3 is a flow chart showing an example of a method according to the first embodiment.

A method of manufacturing recycled pulp fibers from a mixture of pulp fibers and superabsorbent polymer separated from an used sanitary product will now be described. FIG. 3 is a flow chart showing an example of the method according to the first embodiment. The method comprises an ozone treatment step S19, and preferably also comprises a perforating step S11, a shredding step S12, a first separating step S13, a first dust removing step S14, a second dust removing step S15, a third dust removing step S16, a second separating step S17, a third separating step S18 and a fourth separating step S20. These will now be explained.

The perforating step S11 is carried out by the bag tearing apparatus 11. Collection bags A enclosing used sanitary products are loaded into the solution tank V holding the inactivating aqueous solution, and holes are opened in the surfaces of the collection bags that contact with the inactivating aqueous solution. When holes have been opened in the collection bags, the inactivating aqueous solution surrounds and seals the collection bags so that the contaminants, bacteria and odors of the used sanitary products in the collection bags are not released to the outside. When the inactivating aqueous solution infiltrates into the collection bags through the holes, gas inside the collection bags leaks out of the collection bags A, causing the specific gravity of the collection bags to be heavier than the inactivating aqueous solution, so that the collection bags settle more deeply in the inactivating aqueous solution of the solution tank. The inactivating aqueous solution inactivates the superabsorbent polymer in the used sanitary products inside the collection bags.

By inactivation of the superabsorbent polymer in the used sanitary products, whereby its water-absorbing capacity decreases, the superabsorbent polymer becomes dewatered and its particle size is reduced. The pulp fibers containing the superabsorbent polymer are therefore more manageable in each of the subsequent steps, and the treatment efficiency is improved.

The inactivating aqueous solution may be an acidic aqueous solution, or an aqueous solution containing a polyvalent metal ion.

When an acidic aqueous solution (such as an aqueous solution containing an inorganic acid or organic acid) is used as the inactivating aqueous solution, it is possible to lower the ash content of the recycled pulp fibers compared to using an aqueous solution containing a polyvalent metal ion, while it is also easier to adjust the degree of inactivation of the superabsorbent polymer (the particle size and specific gravity) by the pH.

The pH of the acidic aqueous solution is preferably 1.0 or higher and 4.0 or lower, and more preferably 1.2 or higher and 2.5 or lower. If the pH is too high it will not be possible to adequately lower the water-absorbing capacity of the superabsorbent polymer, and the sterilizing power can potentially be lowered as well. If the pH is too low there will be a risk of corrosion of the equipment, and large amounts of alkaline chemicals will be necessary for neutralizing treatment during waste water treatment. In order to separate the pulp fibers and superabsorbent polymer from the other material, it is particularly preferred for the pulp fiber size and specific gravity and the superabsorbent polymer size and specific gravity to be relatively similar. By adjusting the pH of the acidic aqueous solution to 1.0 or higher and 4.0 or lower, the superabsorbent polymer can be reduced even further by inactivation, so that the fiber size and specific gravity of the pulp fibers and the superabsorbent polymer can be made relatively similar.

Examples of organic acids include citric acid, tartaric acid, gluconic acid, glycolic acid and malic acid, with hydroxy carbonate-based organic acids such as citric acid being especially preferred. The chelating effect of citric acid traps metal ions and the like present in excreta, allowing their removal, and the washing effect of citric acid can potentially provide a high fouling-removal effect. Examples of inorganic acids include sulfa is acid, hydrochloric acid and nitric acid, with sulfuric acid being preferred from the viewpoint of cost and the absence of chlorine. The organic acid concentration of the organic acid aqueous solution is not particularly restricted, but when the organic acid is citric acid it is preferably 0.5 mass % or higher and 4 mass % or lower. The inorganic acid concentration of an inorganic acid aqueous solution is also not particularly restricted, but when the inorganic acid is sulfuric acid it is preferably 0.1 mass % or higher and 0.5 mass % or lower.

Throughout the present specification, "pH" means the pH at a temperature of 2.0° C.

The polyvalent metal salts include alkaline earth metal ions and transition metal ions.

The alkaline earth metal ions include beryllium, magnesium, calcium, strontium and barium ions. Preferred for alkaline earth metal ions are calcium chloride, calcium nitrate, calcium hydroxide, calcium oxide, magnesium chloride and magnesium nitrate, with calcium chloride aqueous solution being more preferred.

The transition metal ions are not particularly restricted so long as they can be incorporated into superabsorbent polymers, and they include iron, cobalt, nickel and copper ions. For the transition metal ions there are preferred inorganic acid salts and organic acid salts, from the viewpoint of cost and ready availability. Examples of the inorganic acid salts include iron salts such as iron chloride, iron sulfate, iron phosphate and iron nitrate, cobalt salts such as cobalt chloride, cobalt sulfate, cobalt phosphate and cobalt nitrate, nickel salts such as nickel chloride and nickel sulfate, and copper salts such as copper chloride and copper sulfate. Examples of the organic acid salts include iron lactate, cobalt acetate, cobalt stearate, nickel acetate and copper acetate.

The shredding step S12, first separating step S13, first dust removing step S14, second dust removing step S15, third dust removing step S16, second separating step S17 and third separating step S18 are carried out by the shredding apparatus 12, first separating device 13, first dust removing device 14, second dust removing device 15, third dust removing device 16, second separating device 17 and third separating device 18, respectively, but since these steps have been explained in connection with the apparatuses, they will not be explained here.

The ozone treatment step S19 is carried out by the ozone treatment device 19. The pulp fibers in the solid and the crushed superabsorbent polymer (mixture 98) that have been fed out from the third separating device 18 are treated with an aqueous solution comprising ozone. This causes the superabsorbent polymer to be oxidatively decomposed and removed from the pulp fiber. As a result, the superabsorbent polymer that was adhering on the pulp fibers of the mixture 98 (for example, remaining on the surfaces of the individual pulp fibers) is oxidatively decomposed by the aqueous solution (treatment solution) containing the ozone, being converted to low-molecular-weight organic material that is soluble in the aqueous solution, and being removed from the pulp fiber. Ozone treatment also causes the protein-containing components adhering onto the surfaces and interiors of the pulp fibers to be decomposed, so that the protein-containing components that are capable of eluting into water are removed from the pulp fibers (recycled pulp fibers).

In the ozone treatment step S19, the ozone treatment device 19 shown in FIG. 2 carries out a pretreatment supply step S19-1a, pretreatment step S19-1b and pretreatment solution transfer step S19-1c by the pretreatment apparatus 19-1, and further carries out a supply step S19-2a and treatment step S19-2b by the treatment apparatus 19-2.

The pretreatment supply step S19-1a supplies the mixture 98 into the pretreatment solution P1 in the pretreatment tank 101.

In the pretreatment step S19-1b carried out in the pretreatment tank 101, ozone Z1 is dissipated by the ozone dissipating unit 102a in the pretreatment tank 101 from below the mixture 98, toward the mixture 98 that has separated from the base of the pretreatment tank 101 and is present in the pretreatment solution P1, thus reducing the superabsorbent polymer in the mixture 98.

The pretreatment solution transfer step S19-1c extracts at least a portion of the pretreatment solution P1 containing the mixture 98 with reduced superabsorbent polymer in the pretreatment step S19-1b, from the bottom of the pretreatment tank 101, and transfers it to the treatment solution P2 through the top of the pretreatment tank 101.

Specifically, this takes place as follows.

In the pretreatment supply step S19-1a, water is added to the mixture 98 that contains separated pulp fibers (with residual superabsorbent polymer) in the third separating step S18, producing an aqueous solution. The aqueous solution is supplied from the supply port 101a at the top of the pretreatment tank 101 into the pretreatment solution P1, by the pump 121 through the piping 131, 132 (V1 open, V2 closed).

In the subsequent pretreatment step S19-1b, the pretreatment solution P1 is an acidic aqueous solution (to inhibit inactivation of the ozone and to inactivate the superabsorbent polymer), and it usually has a specific gravity of 1. Therefore, the pulp fibers gradually settle from the top toward the bottom of the pretreatment solution P1. At the same time, the ozone Z1 containing the ozone generated by the ozone generating unit 102b is dissipated into the pretreatment tank 101 from the ozone dissipating unit 102a, through the piping 133. The ozone Z1 is continuously dissipated in a state of fine bubbles (for example, microbubbles or nanobubbles) in the pretreatment solution P1 near the bottom of the pretreatment tank 101, and rises from the bottom toward the top of the pretreatment solution P1.

Inside the pretreatment solution P1, the pulp fibers that settle from top to bottom and the ozone Z1 that rises front bottom to top then proceed in opposite directions and impact each other. The ozone Z1 also adheres to the surfaces of the individual pulp fibers, enveloping the pulp fibers. During this time, the ozone in the ozone Z1 reacts with the superabsorbent polymer in the pulp fibers, whereby the superabsorbent polymer is oxidatively decomposed and dissolved in the pretreatment solution P1. The countercurrent flow can increase the likelihood of contact between the superabsorbent polymer in the pulp fibers and the ozone Z1. The superabsorbent polymer in the pulp fibers is thereby reduced and the viscosity of the superabsorbent polymer-containing pulp fibers is lowered. In the treatment step S19-2b of the later-stage, therefore, it is possible to prevent clogging of the ejector 107 by the superabsorbent polymer-containing pulp fiber.

Next, in the pretreatment solution transfer step S19-1c, at least a portion of the pretreatment solution P1 containing the mixture 98 with reduced superabsorbent polymer in the pretreatment step S19-1b, is extracted from the outlet 101c at the bottom of the pretreatment tank 101 by the pump 122, through the piping 135, and is supplied from the supply port 105a at the top of the treatment tank 105 into the treatment solution P2. The ozone in the ozone-containing ozone Z1 that has accumulated at the top of the pretreatment tank 101 is decomposed and detoxified by the ozone decomposer 103, and is released to the outside.

However, the pretreatment supply step S19-1a may also have a step in which at least a portion of the pretreatment solution P1 containing the mixture is extracted from the bottom of the pretreatment tank 101 and supplied from the top of the pretreatment tank 101 into the pretreatment solution P1. Specifically, using the pump 121, at least a portion of the pretreatment solution P1 containing the mixture is drawn out from the outlet 101b at the bottom of the pretreatment tank 101 through the piping 131, 132 (V1 closed, V2 open), and is supplied from the supply port 101a at the top of the pretreatment tank 101 into the pretreatment solution P1.

The supply step S19-2a supplies the aqueous solution containing the mixture 98 to the driving fluid supply port DI of the ejector 107, while supplying the ozone Z2 to the suction fluid supply port AI of the ejector 107.

In the treatment step S19-2b, the liquid mixture 98L in which the aqueous solution and ozone Z2 have been mixed in the ejector 107 is discharged into the treatment solution P2 in the treatment tank 105, through the mixed fluid discharge port CO of the ejector 107 that is connected at the bottom of the treatment tank 105, thus reducing the superabsorbent polymer in the mixture 98.

Specifically, this takes place as follows, in the pretreatment solution transfer step S19-1c, at least a portion of the pretreatment solution P1 containing the mixture 98 with reduced superabsorbent polymer is supplied into the treatment solution P2 of the treatment tank 105, and the mixture 98 settles in the treatment solution P2, and included in the treatment solution P2. The treatment solution P2 is an acidic aqueous solution (to inhibit deactivation of the ozone and to inactivate the superabsorbent polymer), and it usually has a specific gravity of 1.

In the supply step S19-2a, at least a portion of the treatment solution P2 containing the mixture 98 is drawn out from the bottom of the treatment tank 105, and is supplied to the driving fluid supply port DI as an aqueous solution. Specifically, at least a portion of the treatment solution P2 containing the pretreatment solution P1 that includes the mixture 98 is drawn out from the outlet 105b at the bottom of the treatment tank 105 by the pump 123, through the piping 136, and is supplied to the driving fluid supply port DI of the ejector 107 as an aqueous solution. The ozone Z2 containing the ozone generated at the ozone supply apparatus 106 is then supplied to the suction fluid supply port AI of the ejector 107 through the piping 137.

In the subsequent treatment step S19-2b, the treatment solution P2 containing the mixture 98 and the ozone Z2 are mixed at the ejector 107, and the liquid mixture 98L that is produced is discharged from the mixed fluid discharge port CO into the treatment solution P2 in the treatment tank 105. Since the ozone Z2 and the treatment solution P2 containing the mixture 98 are mixed in an extremely narrow zone in the ejector 107 during this time, an extremely dense liquid mixture 98L of the ozone Z2 and the mixture 98 of the pulp fibers and superabsorbent polymer can be formed.

Discharge of the liquid mixture 98L into the treatment solution P2 in the treatment tank 105 allows the treatment solution P2 to be agitated. Since the ozone Z2 is discharged into the treatment solution P2 in a continuous manner as fine bubbles (for example, microbubbles or nanobubbles) when it is discharged, it is possible to diffuse it over a very wide area in the treatment solution P2. This can very highly increase the likelihood of contact between the superabsorbent polymer in the pulp fibers in the treatment tank 105, and the ozone in the ozone Z2. The superabsorbent polymer is thereby removed from the pulp fiber. It also causes the protein-containing components adhering onto the surfaces and interiors of the pulp fibers to be decomposed, so that the protein-containing components that are capable of eluting into water are removed from the pulp fibers (recycled pulp fibers).

Next, at least a portion of the treatment solution P2 containing the pulp fibers from which the superabsorbent polymer has been removed in the treatment step S19-2b is drawn out from the outlet 105d at the bottom of the treatment tank 105 by the pump 124, through the piping 139, and is transferred to the later-stage devices as a liquid mixture 99. The ozone in the ozone-containing ozone Z2 that has accumulated at the top of the treatment tank 105 is decomposed and detoxified by the ozone decomposer 108, and is released to the outside.

When the ozone-containing ozone Z1, Z2 is supplied to the pretreatment solution P1 and treatment solution P2, the ozone concentration in the pretreatment solution P1 and treatment solution P2 may be 1 to 50 ppm by mass, for example. The ozone concentration in the ozone Z1, Z2 may be 40 to 200 $g/m^3$, for example. The concentration of the pulp fibers (including superabsorbent polymer) in the ozone Z1, Z2 may be 0.1 to 20 mass %, for example. The residence time of the pulp fibers in the pretreatment tank 101 and treatment tank 105 may be 2 minutes to 60 minutes, for example. The ozone Z1, Z2 is preferably supplied into the pretreatment solution P1 and treatment solution P2 in the form of microbubbles or nanobubbles. Microbubbles have bubble diameters of about 1 to 1000 μm, and nanobubbles have bubble diameters of about 100 to 1000 nm.

Since microbubbles or nanobubbles are fine bubbles with large surface areas per unit volume and a slow rising rate in liquid, the likelihood of contact of the bubbles with the pulp fibers is increased, and they can contact with more pulp fiber surfaces. The individual pulp fibers can thus be enveloped in an evenly distributed manner by the fine bubbles, and the contact area between the pulp fibers and the ozone can be further increased. The buoyancy of the fine bubbles also slows the settling rate of the superabsorbent polymer-containing pulp fibers, allowing the contact time between the pulp fibers and the ozone to be further increased. The superabsorbent polymer in the pulp fibers is thus oxidatively decomposed more reliably and removed from the pulp fibers more easily. It also causes the protein-containing components adhering onto the surfaces and interiors of the pulp fibers to be more reliably decomposed, so that the protein-containing components that are capable of eluting into water are more easily removed from the pulp fibers (recycled pulp fibers).

Using an acidic aqueous solution as the treatment solution can inhibit inactivation of the ozone, and can increase the effect of the ozone (oxidative decomposition of the superabsorbent polymer, removal of the protein-containing components, bleaching and deodorization). In addition to inactivating the superabsorbent polymer, using an acidic aqueous solution for the shredding treatment or dust removal treatment allows continuity between each of the treatment steps, without any inconveniences due to differences in the aqueous solution used in different treatment steps, thus allowing the treatment to be carried out in a stable and reliable manner. From the viewpoint of reducing the effect of acid on operating personnel and equipment, an organic acid is preferred for the acidic aqueous solution, with citric acid being preferred from the viewpoint of metal removal.

The fourth separating step S20 is carried out by the fourth separating device 20, whereby the treatment solution containing the pulp fibers that has been treated in the ozone treatment device 19, i.e. the liquid mixture 99, passes through a screen with a plurality of openings and is separated into pulp fibers and treatment solution from the liquid mixture 99. As a result, the treatment solution P2 passes through the screen from the liquid mixture 99 and is separated, and fed out from the fourth separating device 20. The separated treatment solution P2, i.e. the ozone treatment solution, may be returned to the ozone treatment device 19 and reutilized. This can reduce cost for the ozone treatment solution. The pulp fibers in the liquid mixture 99 cannot pass through the screen and remains in the fourth separating device 20, or is fed out separately.

The concentration of ozone in the aqueous solution is measured in the following manner.

(1) Approximately 0.15 g of potassium iodide, 5 mL of a 10 mass % citric acid solution and 85 mL of an ozone-dissolved sample are loaded into a 100 mL graduated cylinder.
(2) After reacting the contents of the graduated cylinder, the reaction product is transferred to a 200 mL Erlenmeyer flask.
(3) A starch solution is added to the Erlenmeyer flask, causing coloration to violet.
(4) The contents of the Erlenmeyer flask are stirred while using 0.01 mol/L sodium thiosulfate for titration until the contents of the Erlenmeyer flask become colorless, and the titer: A (mL) is read off.
(5) The ozone concentration (ppm by mass) in the aqueous solution is calculated by the following formula:

Ozone concentration (ppm by mass) in aqueous solution=$A$(mL)×0.24×0.85 (mL).

Since the ozone Z2 is discharged into the treatment solution P2 in a continuous manner as fine bubbles when it is discharged, it is possible to diffuse it over a very wide area in the treatment solution P2. This allows reaction to proceed very efficiently between the ozone Z2 and the superabsorbent polymer and protein-containing components, with not only the pulp fibers in the liquid mixture 98L discharged from the ejector 107, but also the pulp fibers in the treatment solution in the treatment tank 105. The superabsorbent polymer and protein-containing components in the mixture 98 can also be oxidatively decomposed in a suitable manner, dissolved in the treatment solution P2 and removed, while variation in treatment of the pulp fibers can also be reduced. This can increase the purity of the recycled pulp fibers, allowing production of easily reutilizable recycled pulp fibers. The superabsorbent polymer can thus be suitably removed from the pulp fibers while efficiently producing recycled pulp fibers.

Second Embodiment

According to the second embodiment, the ozone treatment step S19a and ozone treatment device 19a differ from the ozone treatment step S19 and ozone treatment device 19 of the first embodiment. It will be described with focus on this difference.

Figure 4:
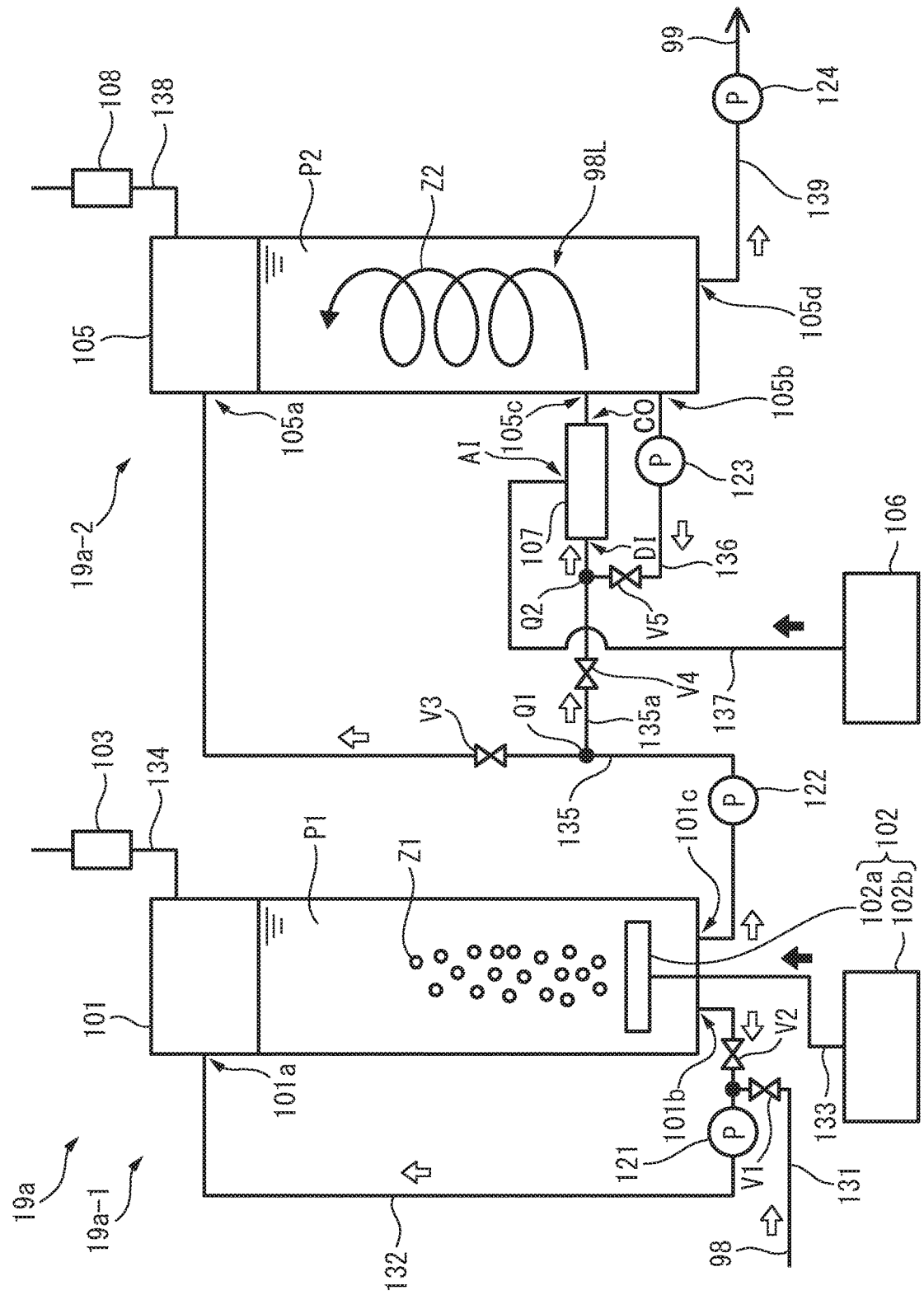
FIG. 4 is a schematic diagram of an ozone treatment device 19a according to a second embodiment.

FIG. 4 is a schematic diagram of the ozone treatment device 19a. The ozone treatment device 19a comprises a pretreatment apparatus 19a-1 and a treatment apparatus 19a-2. The basic construction of the pretreatment apparatus 19a4 and treatment apparatus 19a-2 is the same as the pretreatment apparatus 194 and treatment apparatus 19-2 of the first embodiment. However, they differ in that the piping 135 branches at a branching point Q1 along its length, while the branched pipe 135a merges with the piping 136 at a junction Q2, connecting with the driving fluid supply port DI of the ejector 107. This ozone treatment device 19a thus allows selection of either the treatment tank 105 or ejector 107, or both, as the supply destination of the pretreatment solution P1 of the pretreatment tank 101. The ozone treatment device 19a further comprises, for example, a valve V3 situated downstream from the branching point Q1 along the piping 135, a valve V4 situated along the branched pipe 135a between the branching point Q1 and the junction Q2, and a valve V5 situated upstream from the junction Q2 along the piping 136. Opening and closing of the valve V3, valve V4 and valve V5 allows selection of the supply destination of the pretreatment solution P1 and manner of treatment of the treatment solution P2.

The following cases (A) to (D) are possible for opening and closing of the valves V3, V4 and V5 in the ozone treatment step S19a, where the condition is that either or both the pretreatment solution P1 and treatment solution P2 are supplied to the driving fluid supply port DI of the ejector 107. (A) The valves V3, V4 and V5 are opened, closed, opened, respectively. (B) The valves V3, V4 and V5 are closed, opened, closed, respectively. (C) The valves V3, V4 and V5 are closed, opened, opened, respectively. (D) The valves V3, V4 and V5 are opened, opened, opened, respectively.

In the case of (A), in the pretreatment solution transfer step S19a-1c, the pretreatment solution P1 (containing the mixture 98 that includes the superabsorbent polymer and pulp fibers) in the pretreatment tank 101 is supplied to the supply port 105a of the treatment tank 105 through the piping 135. At the same time, in the supply step S19a-2a, the treatment solution P2 (containing the mixture 98 that includes the superabsorbent polymer and pulp fibers) in the treatment tank 105 is supplied to the driving fluid supply port DI of the ejector 107 through the piping 136. This case is the same as the first embodiment (FIG. 2). It is therefore possible to obtain the same effect as with the first embodiment.

In the case of (B). In the pretreatment solution transfer step S19a-1c, the pretreatment solution P1 in the pretreatment tank 101 is supplied to the driving fluid supply port DI of the ejector 107 through the piping 135 and brandied pipe 135a. The pretreatment solution transfer step S19a-1c is therefore equivalent to the supply step S19a-2a. The treatment solution P2 in the treatment tank 105 is not supplied to the ejector 107 during this time. In this case, all of the pretreatment solution P1 in the pretreatment tank 101 is directly supplied to the driving fluid supply port DI of the ejector 107, unlike the first embodiment (FIG. 2), i.e. the case of (A). Since all of the pulp fibers therefore pass through the ejector 107, all of the pulp fibers can be contacted with the ozone Z2 at the ejector 107, and the treatment efficiency for removal of the superabsorbent polymer can be improved.

In the case of (C), in the pretreatment solution transfer step S19a-1c, the pretreatment solution P1 in the pretreatment tank 101 is supplied to the driving fluid supply port DI of the ejector 107 through the piping 135 and brandied pipe 135a. The pretreatment solution transfer step S19a-1c is therefore equivalent to the supply step S19a-2a. In the supply step S19a-2a, the treatment solution P2 (containing the superabsorbent polymer and pulp fibers) in the treatment tank 105 is supplied to the driving fluid supply port DI of the ejector 107 through the piping 136. In this case, the treatment solution P2 in the treatment tank 105 is also supplied to the driving fluid supply port DI of the ejector 107, unlike in the case of (B). Therefore, at least a portion of the pulp fibers that has passed through the ejector 107 once can be passed through the ejector 107 again. In other words, at least a portion of the pulp fibers can be contacted several times with the ozone Z2 at the ejector 107, allowing the treatment efficiency for removal of the superabsorbent polymer to be further improved.

In the case of (D), in the pretreatment solution transfer step S19a-1c, the pretreatment solution P1 in the pretreatment tank 101 is supplied to the supply port 105a of the treatment tank 105 through the piping 135. At the same time, in the supply step S19a-2a, the pretreatment solution P1 in the pretreatment tank 101 is supplied to the driving fluid supply port DI of the ejector 107 through the piping 135 and branched pipe 135a. In the supply step S19a-2a, the treatment solution P2 (containing the superabsorbent polymer and pulp fibers) in the treatment tank 105 is supplied to the driving fluid supply port D1 of the ejector 107 through the piping 136. In this case, a portion of the pretreatment solution P1 in the pretreatment tank 101 is directly supplied to the driving fluid supply port DI of the ejector 107, unlike the first embodiment (FIG. 2), i.e. the case of (A). Since a portion of the pulp fibers therefore reliably passes through the ejector 107, a portion of the pulp fibers can be reliably contacted with the ozone Z2 at the ejector 107, and the treatment efficiency for removal of the superabsorbent polymer can be improved.

Third Embodiment

According to the third embodiment, the ozone treatment step S19b and ozone treatment device 19b differ from the ozone treatment step S19 and ozone treatment device 19 of the first embodiment. It will be described with focus on this difference.

Figure 5:
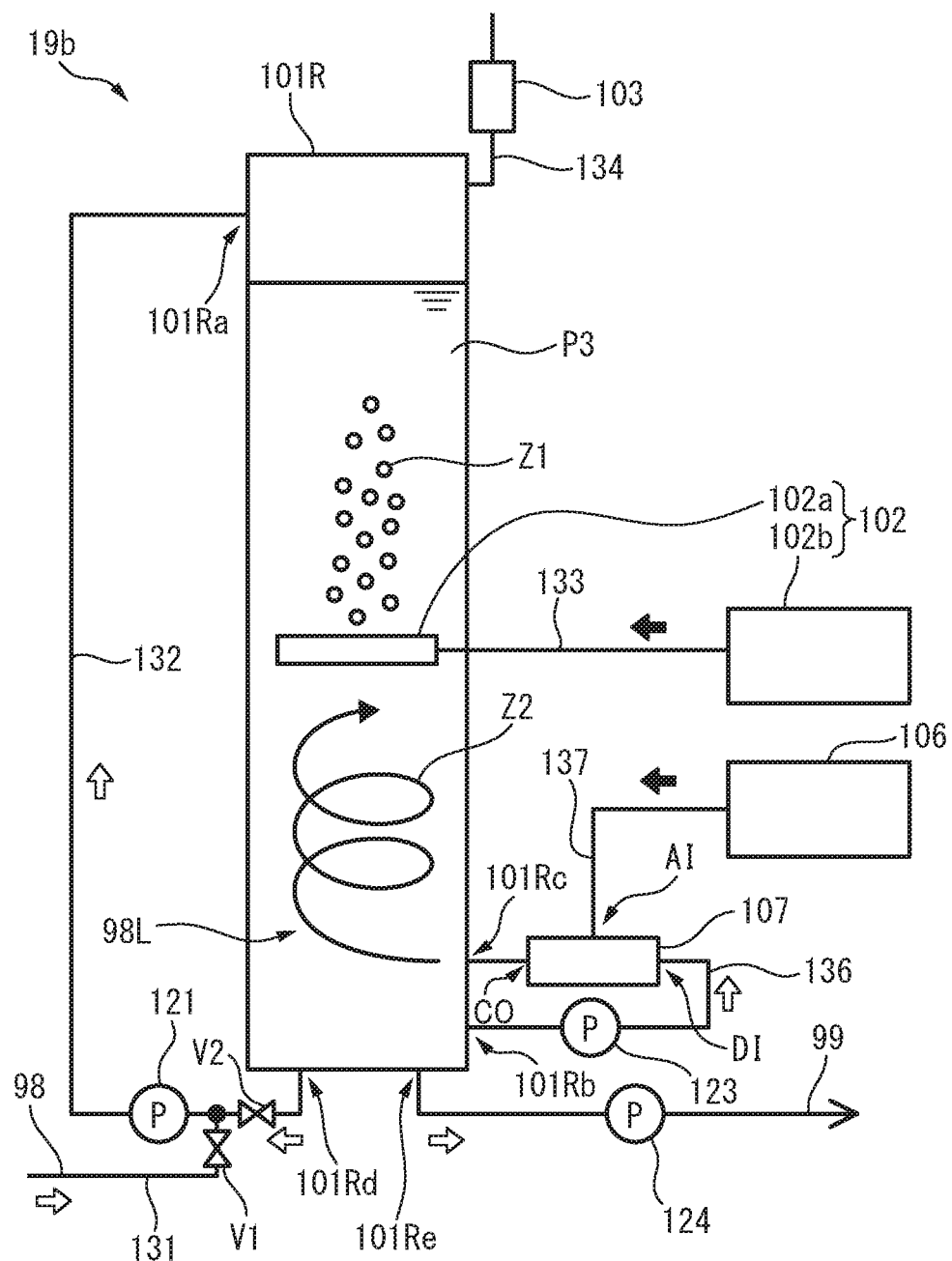
FIG. 5 is a schematic diagram of an ozone treatment device 19b according to a third embodiment.

FIG. 5 is a schematic diagram of the ozone treatment device 19b. The ozone treatment device 19b differs from the ozone treatment device 19 of the first embodiment in that the pretreatment apparatus and the (main) treatment apparatus are integrated. That is, the pretreatment tank and the treatment tank are the same tank 101R. The pretreatment solution and treatment solution are the same solution P3. The mixed fluid discharge port CO of the ejector 107 is situated at a lower section of the tank 101R than the ozone dissipating unit 102a. The pretreatment step S19-1b is carried out at the upper end of the tank while the treatment step S19-2b is carried out at the lower end of the tank, which eliminates the need for part of the space of the pretreatment tank (or treatment tank), as well as the space of the piping 135 connecting the pretreatment tank and treatment tank, so that space is thus reduced in the ozone treatment device 19b.

With the third embodiment it is possible to carry out the pretreatment step S19-1b and the treatment step S19-2b in the same tank, so that there is no need for transfer of the mixture 98 that has been through the pretreatment step S19-1b, to another tank in order to carry out the treatment step S19-2b, and the treatment efficiency can therefore be increased.

<Evaluation Step>

In the evaluation step, the cleanliness of the recycled material is evaluated by a predetermined cleanliness evaluation method.

The predetermined cleanliness evaluation method is the same as the "method of evaluating the cleanliness of a recycled material", and will not be explained here.

For the present disclosure, the sanitary product is not particularly restricted so long as they absorb protein-containing components, and examples include disposable diapers, urine-absorbing pads, sanitary napkins, sanitary shorts, bed sheets, pet sheets and food-wrapping sheets.

The purposes that involve contact with water, according to the disclosure, may be non-water-absorption purposes where contact with water occurs but the water is not intended to be absorbed, or water-absorption purposes where contact with water occurs and the water is intended to be absorbed.

Examples of the non-water-absorption purposes include corrugated boards, and paper (printing paper, wrapping paper, books and magazines).

Examples of the water-absorption purposes include disposable diapers, urine-absorbing pads, sanitary napkins, sanitary shorts, bed sheets, pet sheets, food-wrapping sheets and wet tissues.

<Recycled Pulp Fibers>

The recycled pulp fibers obtained from an used sanitary product according to the disclosure include protein at 60 µg/mL or lower, as measured by the Modified Lowry method. This means that the used sanitary product-derived protein-containing components include an extremely small amount of those that are capable of eluting into water, thus allowing their use not only for water-absorption purposes but also for purposes that involve contact with water. The recycled pulp fibers can also provide a feeling of assurance for users using the recycled pulp fiber.

As used herein, "elution" means that components of interest migrate into aqueous solution in any manner such as dissolution or dispersion.

The protein concentration in the recycled pulp fibers is measured in the following manner.

(1) A Modified Lowry Protein Assay Kit (hereunder also referred to as "ML Kit") by Thermo Fisher Scientific is prepared.
(2) A 500 g portion of an aqueous dispersion containing recycled pulp fibers at a solid concentration of 5.0 mass % is prepared in a 1 liter beaker.

When the recycled pulp fibers are in a dry state, the aqueous dispersion can be formed by mixing the recycled pulp fibers (25.0 g as solid content) and deionized water (for a total amount of 500.0 g). When the recycled pulp fibers are in the form of an aqueous solution (for example, when the recycled pulp fibers have been recovered as an aqueous solution in a method of manufacturing recycled pulp fibers), and the solid concentration of the recycled pulp fibers is 5.0 mass % or greater, deionized water may be added to the aqueous solution to prepare an aqueous dispersion with the recycled pulp fibers at a solid concentration of 5.0 mass %.

When the recycled pulp fibers are in the form of an aqueous solution and the solid concentration of the recycled pulp fibers is less than 5.0 mass %, filtration may be carried out to adjust the solid concentration of the recycled pulp fibers to 5.0 mass %.

For this purpose, the solid content (for example, the solid content of the recycled pulp fibers) and the solid concentration (for example, the solid concentration of the recycled pulp fibers in the aqueous dispersion) can be measured by drying a partial fraction thereof at 105° C. for 16 hours. The actual sample used for measurement of the solid content and solid concentration (for example, the actual recycled pulp fibers) will have a thermal history, and therefore it is not used for measurement of the protein concentration.

This solid concentration, incidentally, is stipulated in light of the fact that the aqueous dispersion also includes impurities other than the recycled pulp fiber.

As used herein, the solid content and solid concentration can be measured by the following formula:

Solid content (mass %), solid concentration (mass %)=100×$m_1/m_0$, where $m_0$ (g) is for the sample (for example, the recycled pulp fibers and aqueous dispersion), and $m_1$ (g) is for the residue obtained by drying under the conditions specified above.

(3) The aqueous dispersion is stirred for 15 minutes at a rotational speed of 300 rpm, using an overhead stirrer.

(4) A Micro Refrigerated Centrifuge Model 3740 by Kubota Corp. is prepared. The aqueous dispersion that has been stirred with the overhead stirrer is centrifugally separated for 5 minutes under conditions of 12,000 rpm, 4° C., and the supernatant is collected.

(5) The protein concentration in the supernatant is measured using the ML Kit. The protein concentration is measured according to "Test Tube Procedure" in the "INSTRUCTIONS" for the ML Kit.

When the supernatant includes substances that interfere with measurement of the protein concentration with the ML Kit, the effects of the interfering substances can be eliminated by the methods described in the ML Kit, such as dialysis, gel filtration, sample dilution, or protein precipitation using acetone or trichloroacetic acid.

The absorbance is measured using a Model UV-2450 ultraviolet and visible spectrophotometer by Shimadzu Corp.

The measurement is carried out at room temperature, and preferably 25° C.

The recycled pulp fibers of the disclosure has no detection of preferably *Bacillus cereus* and *Bacillus subtilis*, more preferably no detection of *Bacillus bacteria*, and even more preferably no detection of bacteria, as measured by a pour culture method.

*Bacillus* strains such as *Bacillus cereus* and *Bacillus subtilis* are resident flora generally present in soil, water and plants, and because they form spores they are very highly durable bacteria. Spores are highly resistant against heat and disinfectants and often cannot be completely removed by common disinfection methods, in some rare cases even causing bacteremia, endocarditis, respiratory infection, food poisoning or eye infection.

Bacteria that can be detected by the pour culture method include common viable bacteria such as *Bacillus cereus*, *Bacillus subtilis*, *Staphylococcus aureus*, *Pseudomonas aeruginosa*, glucose non-fermenting bacilli and *Aeromonas* bacteria.

If bacteria are not detected by pour culture, then the recycled pulp fibers will be unlikely to cause bacteremia, endocarditis, respiratory infection, food poisoning or eye infection, and the user can use the recycled pulp fibers without concern.

The recycled pulp fibers of the disclosure preferably have no detection of bacteria, and specifically enterobacteria, by the plate culture method. This can lower the risk of opportunistic infection and allow the recycled pulp fibers to be used without concern.

Examples of enterobacteria include *Escherichia coli*, *Klebsiella oxytoca*, *Citrobacter freundii*, *Klebsiella* spp., *Klebsiella pneumoniae*, *Enterobacter cloacae*, *Proteus mirabilis*, *Enterobacter* spp., *Enterobacter aerogenes*, *Morganella morganii* and *Providencia rettgeri*.

The culture method, including the plate culture method or pour culture method, is carried out in the following manner.

(1) A 500 g portion of an aqueous dispersion containing recycled pulp fibers at a solid concentration of 5.0 mass % is prepared in a 1 liter beaker.

When the recycled pulp fibers are in a dry state, the aqueous dispersion can be formed by mixing the recycled pulp fibers (25.0 g as solid content) and deionized water (for a total amount of 500.0 g). When the recycled pulp fibers is in the form of an aqueous solution (for example, when the recycled pulp fibers have been recovered as an aqueous solution in a method of manufacturing recycled pulp fibers), and the solid concentration of the recycled pulp fibers is 5.0 mass % or greater, deionized water may be added to the aqueous solution to prepare an aqueous dispersion with the recycled pulp fibers at a solid concentration of 5.0 mass %.

When the recycled pulp fibers are in the form of an aqueous solution, and the solid concentration of the recycled pulp fibers is less than 5.0 mass %, either the solid concentration of the recycled pulp fibers may be adjusted to 5.0 mass % by filtration, or the aqueous solution itself may be used as the aqueous dispersion and the inoculation volume of a serially diluted sample (described below) may be increased (for example, an inoculation volume of 2-fold when the solid concentration of the recycled pulp fibers is 2.5 mass %).

(2) The aqueous dispersion is stirred for 15 minutes at a rotational speed of 300 rpm, using an overhead stirrer.

(3) A 50 mL portion of an aqueous dispersion that has been stirred with an overhead stirrer is placed in a filter-equipped sterilization bag (filter-equipped sterilization bag for homogenizer, product of LMS Co.), and stirred for 5 minutes.

(4) The aqueous dispersion that has been filtered with the filter-equipped sterilization bag is dispensed into a sterilized test tube, serially diluted 10-fold to $10^{-9}$, and dispensed into a sterilized test tube, to prepare serially diluted samples.

(5-1) The enterobacteria count is measured by the plate culture method.

Specifically, 0.1 mL of each serially diluted sample is inoculated into BTB lactose-added agar medium (251251, product of Becton Dickinson, Japan), coating the serially diluted sample with a bacteria spreader, and culturing at 35° C. for 24 hours.

(5-2) The general viable cell count is measured by a pour culture method.

Specifically, 1 mL of serially diluted sample is placed in a dish with standard agar medium ("Daigo" 396-00175SM agar medium for general viable cell counting, product of Nihon Pharmaceutical Co., Ltd., 15-20 g), and pour culture is carried out at 35° C. for 48 hours.

(6) The number of colonies that have developed is counted after culturing, for both the enterobacteria count and the general viable cell count.

When the number of colonies is zero for all of the serially diluted samples that had been serially diluted 10-fold to $10^{-9}$, the bacteria of interest are judged to be "undetected".

(7) When colonies of enterobacteria or general viable bacteria have formed after culturing, the type of bacteria can be identified. The identification may be done by examination of the biochemical properties.

The recycled pulp fibers of the disclosure have a ΔYI of preferably 0 to 20, more preferably 0 to 15 and even more preferably 0 to 10, against a standard white board. This will make it unlikely for the user to experience a feeling of psychological resistance against an article using the recycled pulp fiber.

The recycled pulp fibers of the disclosure also have a ΔW of preferably 0 to 20, more preferably 0 to 15 and even more preferably 0 to 10, against a standard white board. This will make it unlikely for the user to experience a feeling of psychological resistance against an article using the recycled pulp fiber.

The ΔYI and ΔW of the recycled pulp fibers can be measured in the following manner.

(1) After preparing recycled pulp fibers dried at 120° C. for 60 minutes in a constant temperature and humidity room at a temperature of 20±5° C. and a humidity of 65±5% RH, deionized water is added to the recycled pulp fibers to a water content of 50 mass % to form wetted recycled pulp fibers, and the wetted recycled pulp fibers are allowed to stand for 24 hours in a sealed container.

The water content (mass %) is the proportion of deionized water with respect to the recycled pulp fibers that have been dried at 120° C. for 60 minutes.

(2) A color measurement color meter (Model ZE2000, product of Nippon Denshoku Industries Co., Ltd.) is prepared in a constant temperature and humidity room at a temperature of 20±5° C. and a humidity of 65±5% RH.

(3) The glass window (40 min diameter) of the sample stage of the color difference meter is evenly spread with 4.5 g of the wetted recycled pulp fiber.

(4) A black plate (size: 80 mm×80 mm, mass: 280 g) included in the color difference meter is placed on the spread recycled pulp fiber, and a load is applied onto the recycled pulp fiber.

(5) The YI value and W value of the recycled pulp fibers are measured with the color difference meter switched to reflection mode and a transmission window diameter of 30 mm, and calculation is performed for ΔYI (=|[YI value of recycled pulp fibers]-[YI value of standard white board]|), which is the color difference (absolute value) from the YI value of the standard white board, and for ΔW (=|[W value of recycled pulp fibers]-[W value of standard white board]|), which is the color difference (absolute value) from the W value of the standard white board.

(6) Using different recycled pulp fibers, ΔYI is measured a total of 10 times, ΔW is measured a total of 10 times, the average ΔYI is measured a total of 10 times and the average ΔW is measured a total of 10 limes.

For the present disclosure, a sanitary product may be the same as explained above under "Method of manufacturing recycled material from an used sanitary product".

The purposes that involve contact with water, according to the disclosure, may be non-water-absorption purposes where contact with water occurs but the water is not intended to be absorbed, or water-absorption purposes where contact with water occurs and the water is intended to be absorbed, and specific examples include the same ones mentioned above under "Method of manufacturing a recycled material from an used sanitary product".

The method of manufacturing the recycled pulp fibers of the disclosure is not particularly restricted so long as it includes protein at the predetermined concentration, and for example, it may be manufactured according to the embodiments described above under "Method of manufacturing recycled pulp fibers from a pulp fiber-containing used sanitary product".

<Method of Manufacturing Recycled Pulp Fibers>

The method of manufacturing recycled pulp fibers from a pulp fiber-containing used sanitary product according to the present disclosure is the same as described under "Recycled material manufacturing method", and will not be explained again here.

EXAMPLES

The present disclosure will now be explained in fuller detail by examples, with the understanding that the disclosure is not meant to be limited to the examples.

As protein measurement means there were prepared a Modified Lowry Protein Assay Kit by Thermo Fisher Scientific (lower quantification limit: 60 μg/mL) for the ML method, a Coomassie (Bradford) Protein Assay Kit (lower quantification limit: 7 μg/mL) for the Coomassie method, and a Micro BCA Protein Assay Kit (lower quantification limit: 7 μg/mL) for the Micro BCA method.

[Production Example 1 and Production Example 2]

Using a SUMICUTTER (product of Sumitomo Heavy Industries Environment Co. Ltd.) as the shredding apparatus, a total of 1400 used disposable diapers (approximately 250 kg) collected from an elderly care facility were shredded to form a shredded matter-containing aqueous solution. The inactivating aqueous solution used was approximately 1 t of a 0.16 mass % calcium hydroxide aqueous solution.

The shredded matter-containing aqueous solution was introduced into an ECO-22B horizontal washing machine (product of Inax Corp.) as the first separating device, and separated into the pulp fibers and superabsorbent polymer and the other constituent material, to form an aqueous solution containing the pulp fibers and superabsorbent polymer. The aqueous solution containing the pulp fibers and superabsorbent polymer was then passed through a first dust removing device, second dust removing device and third dust removing device and transferred to a stirring tank.

A portion of the aqueous solution containing the pulp fibers and superabsorbent polymer in the stirring tank was extracted and adjusted to a solid concentration of 5.0 mass %, as a first extracted sample.

The first extracted sample was centrifugally separated using a Micro Refrigerated Centrifuge (Model 3740 by Kubota Corp., rotational speed: 12,000 rpm, temperature: 4° C., time: 5 minutes), to form sample No. 1 (Production Example 1).

A 2 mass % citric acid aqueous solution was added to the stirring tank in an amount so that 1 part by mass of citric acid was added for 1 part by mass of pulp fiber solid content, the contents of the stirring tank were transferred to an ozone treatment device, ozone treatment and ejector treatment were carried out, and the superabsorbent polymer was decomposed. A portion of the contents that had passed through the ozone treatment device was extracted to form a second extracted sample. The solid concentration of the second extracted sample was approximately 2 mass %. The second extracted sample was dewatered to adjust the solid concentration to about 5 mass %.

In the ozone treatment step using the ozone treatment device, the ozone concentration in the pretreatment step S19-1$b$ was 200 g/m$^3$ and the ozone supply rate was 100 g/h. In the treatment step S19-2$b$, the ozone concentration was 200 g/m$^3$ and the ozone supply rate was 100 g/h.

The second extracted sample with the solid concentration adjusted to about 5 mass % was centrifugally separated using a Micro Refrigerated Centrifuge (Model 3740 by Kubota Corp., rotational speed: 12,000 rpm, temperature: 4° C., time: 5 minutes), to form sample No. 2 (Production Example 2).

[Production Example 3]

Virgin pulp fibers (N9416 by Weyerhaeuser Co.) were dispersed in a 2 mass % citric acid aqueous solution to prepare a virgin pulp fiber-dispersed aqueous solution with a solid concentration of 5.0 mass %, and the virgin pulp fiber-dispersed aqueous solution was subjected to ozone treatment and ejector treatment under the same conditions as Production Example 2. A portion of the treated virgin pulp fiber-dispersed aqueous solution was extracted to form a third extracted sample. The third extracted sample was adjusted to a solid concentration of 5.0 mass %.

The third extracted sample was centrifugally separated using a Micro Refrigerated Centrifuge (Model 3740 by Kubota Corp., rotational speed: 12,000 rpm, temperature: 4° C., time: 5 minutes), to form sample No. 3.

[Production Example 4]

A superabsorbent polymer (AQUA KEEP, by Sumitomo Seika Chemicals Co., Ltd.) was dispersed in a 2 mass % citric acid aqueous solution to prepare a superabsorbent polymer-dispersed aqueous solution with a solid concentration of 5.0 mass %, and the superabsorbent polymer-dispersed aqueous solution was subjected to ozone treatment and ejector treatment under the same conditions as Production Example 2, A portion of the treated superabsorbent polymer-dispersed aqueous solution was extracted to form a fourth extracted sample. The fourth extracted sample contained the decomposed superabsorbent polymer in an amount corresponding to 5 mass % superabsorbent polymer.

The fourth extracted sample was centrifugally separated using a Micro Refrigerated Centrifuge (Model 3740 by Kubota Corp., rotational speed: 12,000 rpm, temperature: 4° C., time: 5 minutes), to form sample No. 4.

[Production Example 5 and Production Example 6]

Bovine serum albumin (BSA) was added to each of sample Nos. 3 and 4 to a BSA concentration of 100 μg/mL (ML method) and 20 μg/mL (Coomassie method and Micro BCA method), to prepare sample Nos. 5 and 6.

[Production Example 7 and Production Example 8]

Of the filtrate and residue obtained by ultrafiltration of sample No. 2, the filtrate alone was used as sample No. 7.

The residue was washed on an ultrafiltration filter using deionized water in an amount approximately equivalent to the filtrate, and the wash fluid was centrifugally separated using a Micro Refrigerated Centrifuge (Model 3740 by Kubota Corp., rotational speed: 12,000 rpm, temperature: 4° C., time: 5 minutes), to form sample No. 8.

Example 1

[Drawing of Calibration Curve]

A calibration curve was drawn by the method described in the Modified Lowry Protein Assay Kit, Coomassie (Bradford) Protein Assay Kit or Micro BCA Protein Assay Kit.

[Measurement of Protein Concentration]

The protein concentrations of samples No. 1 to No. 8 were measured by the ME: method, Coomassie method and Micro BCA method. The results are shown in Table 1.

Specifically, in the ML method, 1.0 mL of Lowry reagent was added to 0.2 mL of sample and the mixture was incubated for 10 minutes at room temperature, after which 100 μg/mL of Folin-Ciocaiteu reagent was added and the mixture was further incubated at room temperature for 30 minutes to prepare a test solution. The absorbance of the test solution at 750 nm was measured with a quartz microcell having an optical path length of 1 cm, using purified water as a control, and the protein concentration was calculated using a calibration curve.

In the Coomassie method, 1.0 mL of Coomassie reagent was added to 1.0 mL of sample, and the mixture was incubated for 10 minutes at room temperature to prepare a test solution. The absorbance of the test solution at 595 nm was measured with a quartz microcell having an optical path length of 1 cm, using purified water as a control, and the protein concentration was calculated using a calibration curve.

In the Micro BCA method, 1.0 mL of BCA Working reagent was added to 1.0 mL of sample and the mixture was incubated for 60 minutes in a water bath at 60° C. to prepare a test solution. The absorbance of the test solution at 562 nm was measured with a quartz macrocell having an optical path length of 1 cm, using purified water as a control, and the protein concentration was calculated using a calibration curve.

For all of the protein measurement means, the absorbance was measured using a Model UV-2450 ultraviolet and visible spectrophotometer by Shimadzu Corp.

TABLE 1

| Sample No. | ML method (μg/mL) | Coomassie method (μg/mL) | Micro BCA method (μg/mL) |
|---|---|---|---|
| 1 | 179.4 | 73.0 | 142.8 |
| 2 | ≤60 | 30.0 | ≤7 |
| 3 | ≤60 | ≤7 | 8.7 |
| 4 | ≤60 | 30.0 | ≤7 |
| 5 | 100.0 | 22.0 | 17.0 |
| 6 | 86.0 | 32.0 | 15.0 |
| 7 | ≤60 | ≤7 | 8.7 |
| 8 | ≤60 | 31.0 | ≤7 |

[ML Method]

In the ML method, the protein concentration was below the detection limit for samples No. 3 and No. 4, while for samples No. 5 and No. 6, the protein concentration was 100 μg/mL, which was approximately the same as the added BSA concentration. In the ML method, no protein was detected in sample No. 7 and sample No. 8, which were derived from sample No. 2 that had protein below the detection limit.

This indicates that the ML method allows easy measurement all at once of the total amount of protein-containing components that are capable of eluting into water from any recycled materials of used sanitary products.

[Coomassie Method]

In the Coomassie method, the protein concentration was below the detection limit for sample No. 3, while for sample No. 5, the protein concentration was 22 μg/mL, which was approximately the same as the added BSA concentration. For sample No. 4, however, the protein concentration was measured to be 30 μg/mL, while for sample No. 6, the protein concentration was detected at a higher concentration than the added BSA, which suggested the presence of factors inhibiting quantitation of protein in sample No. 4 and sample No. 6. With the Coomassie method, protein was undetected from sample No. 7, but protein was detected from sample No. 8.

These results suggest that the decomposed superabsorbent polymer exhibited a protein-like response (false positivity) with the Coomassie method.

In the Coomassie method, a protein concentration of 30.0 μg/mL was detected for sample No. 2, but presumably the decomposed superabsorbent polymer exhibited a protein-like response (false positivity) in sample No. 2 as well.

This indicates that the Coomassie method allows easy measurement all at once of the total amount of protein-containing components capable of eluting into water, from a recycled material of used sanitary products (that do not include a superabsorbent polymer).

[Micro BCA Method]

In the Micro BCA method, the protein concentration was below the detection limit for sample No. 4, while for samples No. 5 and No. 6, the protein concentrations were approximately the same level as the added BSA concentrations. However, protein was detected in sample No. 2 and sample No. 3 which did not contain protein. Since protein was detected from sample No. 7 but not from sample No. 8 in the Micro BCA method, it is thought that the water-soluble components (citric acid functioning as a chelating agent) inhibits detection of protein, by acting as an inhibiting substance that causes false negativity.

This suggests that citric acid can influence quantitation of protein in the Micro BCA method.

Since the protein concentrations of samples No. 5 and No. 6 were measured to be 17.0 μg/mL and 15.0 μg/mL respectively, in the Micro BCA method, this suggests its potential for allowing accurate measurement of protein concentrations.

It is therefore suggested that the Micro BCA method allows easy measurement all at once of the total amount of protein-containing components capable of eluting into water, from a recycled material of used sanitary products (that do not include a chelating agent).

Example 2

Approximately 15 kg of 100 used paper diapers collected from an elderly care facility were loaded into a sterilized stirring container, after which 600 kg of sterilized water was loaded into the stirring container to a concentration of pulp fibers (3 kg) of approximately 5 mass %, and the contents of the container were stirred for 10 minutes and the aqueous solution in the container was used as sample No. 9.

The bacteria counts of sample No. 9 and sample No. 2 were measured by the pour culture method and plate culture method described herein. The results are shown in Table 2. The major types of bacteria were identified by examination of the biochemical properties. The results are shown in Table 2.

In Example 2, sample No. 2 refers to the second extracted sample.

The letters ND in Table 2 stand for "Not Detected".

TABLE 2

| Bacterial strain | Sample No. 9 | Sample No. 2 (second extracted sample) |
|---|---|---|
| General viable bacteria (pour culture method) | 2.04E+11 | 0 |
| Bacillus cereus | | 0 |
| Enterobacteria (plate culture method) | 1.12E+11 | ND[1)] |
| Escherichia coli | 5.80E+10 | ND |
| Klebsiella oxytoca | 2.60E+10 | ND |
| Citrobacter freundii | 1.33E+10 | ND |
| Klebsiella spp. | 6.58E+09 | ND |
| Klebsiella pneumoniae | 4.97E+09 | ND |
| Enterobacter cloacae | 1.18E+09 | ND |
| Proteus mirabilis | 9.27E+08 | ND |
| Enterobacter spp. | 5.92E+08 | ND |
| Enterobacter aerogenes | 3.95E+08 | ND |
| Morganella morganii | 1.28E+08 | ND |
| Providencia rettgeri | 1.22E+08 | ND |
| | | ND |
| Other | 8.70E+09 | ND |
| Pseudomonas aeruginosa | 5.43E+09 | ND |
| Aeromonas hydrophila | 2.45E+09 | ND |
| GNFR[2)] | 8.14E+08 | ND |

[1)]Not detected
[2)]Glucose non-fermentative gram-negative rods

Upon confirmation by examination of the biochemical properties, most of the general viable bacteria in sample No. 9 were found to be *Bacillus cereus*, including some *Bacillus subtilis*. The bacteria count in sample No. 1 (first extracted sample) was measured by the pour culture method, and a bacteria count of 1.39 E+5 was detected. When these were identified by examination of the biochemical properties, *Bacillus cereus* and *Bacillus subtilis* were found to be present in sample No. 1 (first extracted sample).

No *Bacillus cereus* or *Bacillus subtilis* were detected in sample No. 2 (second extracted sample).

Example 3

The ΔW and ΔYI values for the (recycled) pulp fibers were measured for sample No. 1, sample No. 2 and sample No. 3. The results are shown in Table 3.

In Example 3, sample No. 1 and sample No. 2 are (recycled) pulp fibers obtained by drying the first extracted sample and the second extracted sample, respectively, under the same conditions as for measurement of the solid content, while sample No. 3 is the virgin pulp fibers (NB416 by Weyerhaeuser).

TABLE 3

| | Sample No. 1 | Sample No. 2 | Sample No. 3 |
|---|---|---|---|
| ΔW | 25 | 14 | 13 |
| ΔYI | 25 | 3 | 16 |

REFERENCE SIGNS LIST

19 Ozone treatment device
19-2a Supply step
19-2b Treatment step
98 Mixture
105 Treatment tank
107 Ejector
AI Suction fluid supply port
CO Mixed fluid discharge port
DI Driving fluid supply port
P2 Treatment solution
Z2 Ozone

The invention claimed is:

1. A method of manufacturing a recycled material from an used sanitary product, wherein the method includes:
   a recycling step of forming the recycled material from the used sanitary product and
       an evaluation step of evaluating the cleanliness of the recycled material by the following method
   a provision step of providing a dispersed aqueous solution having the recycled material dispersed in water,
   a separation step of separating the dispersed aqueous solution into a liquid component and a solid component by centrifugal separation, and
a measurement step of measuring a concentration of protein in the liquid component by protein measurement means.

2. A method of manufacturing recycled pulp fibers from a pulp fiber-containing used sanitary product, wherein the method includes:
   a supply step of supplying an aqueous solution containing the pulp fibers to a driving fluid supply port of a treatment tank provided with an ejector, the ejector comprising the driving fluid supply port, a mixed fluid discharge port connected to the treatment tank, and a suction fluid supply port between them, while supplying ozone to the suction fluid supply port, and a recycled pulp fiber-forming step of forming recycled pulp fibers by discharging a liquid mixture formed by mixing of the aqueous solution and the ozone in the ejector into the treatment solution in the treatment tank from the mixed fluid discharge port, and decomposing the protein-containing components in the pulp fibers such that an aqueous dispersion comprising the recycled pulp fibers dispersed at a solid concentration of 5.0 mass % contains protein at a concentration of 60 µg/mL or lower, as measured by a Modified Lowry method.

3. The method according to claim 2, wherein the used sanitary product further includes a superabsorbent polymer, the aqueous solution further includes the superabsorbent polymer in the supply step, and the superabsorbent polymer is further decomposed in the recycled pulp fiber-forming step.

4. The method according to claim 3, wherein the manufacturing method includes, before the supply step, an inactivating step of inactivating the superabsorbent polymer by an acidic aqueous solution.

5. The method according to claim 2, wherein an ozone concentration in the solution is 1 to 50 ppm by mass.

6. The method according to claim 2, wherein an ozone concentration in the solution is 40 to 200 $g/m^3$.

* * * * *